US012760347B2

(12) United States Patent
Chen et al.

(10) Patent No.: US 12,760,347 B2
(45) Date of Patent: Oct. 13, 2026

(54) CELL CULTURE PROCESS FOR MAKING A GLYCOPROTEIN

(71) Applicant: Regeneron Pharmaceuticals, Inc., Tarrytown, NY (US)

(72) Inventors: John Chen, East Greenblush, NY (US); Shawn Lawrence, Nyack, NY (US); Amy Johnson, Briarcliff Manor, NY (US); Theodore Loney, Averill Park, NY (US); Ravindra Pangule, Bridgewater, NJ (US); Ta-Chun Hang, Cambridge, MA (US); Scott Carver, Wynantskill, NY (US); Bernhard Schilling, Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1134 days.

(21) Appl. No.: 17/409,158

(22) Filed: Aug. 23, 2021

(65) Prior Publication Data

US 2021/0388407 A1 Dec. 16, 2021

Related U.S. Application Data

(62) Division of application No. 16/026,539, filed on Jul. 3, 2018, now abandoned.

(60) Provisional application No. 62/625,744, filed on Feb. 2, 2018, provisional application No. 62/529,471, filed on Jul. 6, 2017.

(51) Int. Cl.

| | |
|---|---|
| ***C12P 21/00*** | (2006.01) |
| ***C07K 14/47*** | (2006.01) |
| ***C07K 14/71*** | (2006.01) |
| ***C07K 14/715*** | (2006.01) |

(52) U.S. Cl.

CPC ........ *C12P 21/005* (2013.01); *C07K 14/4705* (2013.01); *C07K 14/71* (2013.01); *C07K 14/7155* (2013.01); *C07K 2319/30* (2013.01); *C07K 2319/32* (2013.01)

(58) Field of Classification Search

CPC ....... C12P 21/005; C12P 21/06; C12N 5/0018
See application file for complete search history.

(56) References Cited

U.S. PATENT DOCUMENTS

| | | | |
|---|---|---|---|
| 4,072,565 | A | 2/1978 | Weiss et al. |
| RE30,985 | E | 6/1982 | Cartaya et al. |
| 4,560,655 | A | 12/1985 | Baker |
| 4,615,977 | A | 10/1986 | Hasegawa et al. |
| 4,657,866 | A | 4/1987 | Kumar |
| 4,786,599 | A | 11/1988 | Chessebeuf et al. |
| 5,063,157 | A | 11/1991 | Stockinger |
| 5,122,469 | A | 6/1992 | Mather et al. |
| 5,342,777 | A | 8/1994 | Cole et al. |
| 5,426,699 | A | 6/1995 | Wunderlich et al. |
| 5,529,920 | A | 6/1996 | Cole et al. |
| 5,610,279 | A | 3/1997 | Brockhaus et al. |
| 5,705,364 | A | 1/1998 | Etcheverry et al. |
| 5,811,299 | A | 9/1998 | Renner et al. |
| 5,856,179 | A | 1/1999 | Chen et al. |
| 5,976,833 | A | 11/1999 | Furukawa et al. |
| 6,043,092 | A | 3/2000 | Block |
| 6,048,728 | A | 4/2000 | Inlow et al. |
| 6,087,123 | A | 7/2000 | Wissler et al. |
| 6,146,847 | A | 11/2000 | Goffe et al. |
| 6,180,401 | B1 | 1/2001 | Chen et al. |
| 6,528,286 | B1 | 3/2003 | Ryll |
| 6,589,759 | B1 | 7/2003 | Loscalzo et al. |
| 6,924,124 | B1 | 8/2005 | Singh |
| 6,927,004 | B2 | 8/2005 | Eurlings et al. |
| 7,070,959 | B1 | 7/2006 | Papadopoulos et al. |
| 7,087,411 | B2 | 8/2006 | Daly et al. |

(Continued)

FOREIGN PATENT DOCUMENTS

| | | | |
|---|---|---|---|
| CN | 1241573 | A | 1/2000 |
| CN | 1367258 | A | 9/2002 |

(Continued)

OTHER PUBLICATIONS

Richardson J, Shah B, Bondarenko PV, Bhebe P, Zhang Z, Nicklaus M, Kombe MC. Metabolomics analysis of soy hydrolysates for the identification of productivity markers of mammalian cells for manufacturing therapeutic proteins. Biotechnol Prog. Mar.-Apr. 2015;31(2):522-31. (Year: 2015).*

(Continued)

*Primary Examiner* — Fereydoun G Sajjadi
*Assistant Examiner* — Qinhua Gu
(74) *Attorney, Agent, or Firm* — Fenwick & West LLP; Matthew Pavao; Jessica D. Cande

(57) ABSTRACT

The instant application provides a method for screening batches of soy hydrolysate for a desired amount of a component thereof, such as ornithine or putrescine, and selecting only those batches of soy hydrolysate that have a desired amount of such component. The present disclosure also sets forth methods for culturing cells in media supplemented with selected batches of soy to produce more consistent, high quality lots of a protein of interest. Further, the present disclosure provides a plurality of protein preparations that have each been produced by culturing cells in media supplemented with separate batches of soy hydrolysate containing a desired amount of ornithine or putrescine, whereby each batch of protein produced exhibits improved quality of the protein of interest or amount of quality protein produced.

16 Claims, 7 Drawing Sheets

Specification includes a Sequence Listing.

(56) References Cited

U.S. PATENT DOCUMENTS

| | | | |
|---|---|---|---|
| 7,105,348 | B2 | 9/2006 | Murphy et al. |
| 7,279,159 | B2 | 10/2007 | Daly et al. |
| 7,294,484 | B2 | 11/2007 | Drapeau et al. |
| 7,303,694 | B2 | 12/2007 | Murphy et al. |
| 7,429,491 | B2 | 9/2008 | Luan et al. |
| 7,435,553 | B2 | 10/2008 | Fandl et al. |
| 7,455,988 | B2 | 11/2008 | Fandl et al. |
| 7,582,298 | B2 | 9/2009 | Stevens et al. |
| 7,666,416 | B2 | 2/2010 | Etcheverry et al. |
| 7,750,138 | B2 | 7/2010 | Fang et al. |
| 7,771,997 | B2 | 8/2010 | Chen et al. |
| 7,879,984 | B2 | 2/2011 | Martin et al. |
| 7,951,577 | B2 | 5/2011 | Murphy et al. |
| 8,021,881 | B2 | 9/2011 | Reiter et al. |
| 8,043,617 | B2 | 10/2011 | Stevens et al. |
| 8,062,640 | B2 | 11/2011 | Sleeman et al. |
| 8,216,575 | B2 | 7/2012 | Yu |
| 8,313,926 | B2 | 11/2012 | Grillberger et al. |
| 8,440,408 | B2 | 5/2013 | Grillberger et al. |
| 8,637,312 | B2 | 1/2014 | Kruger et al. |
| 8,735,095 | B2 | 5/2014 | Martin et al. |
| 8,871,209 | B2 | 10/2014 | Stitt et al. |
| 8,945,559 | B2 | 2/2015 | Dix et al. |
| 9,018,356 | B2 | 4/2015 | Sleeman et al. |
| 9,045,536 | B2 | 6/2015 | Merchant et al. |
| 9,079,948 | B2 | 7/2015 | Orengo et al. |
| 9,127,265 | B2 | 9/2015 | Grillberger et al. |
| 9,132,192 | B2 | 9/2015 | Daly et al. |
| 9,150,645 | B2 | 10/2015 | Subramanian et al. |
| 9,173,880 | B2 | 11/2015 | Dix et al. |
| 9,181,572 | B2 | 11/2015 | Subramanian et al. |
| 9,217,168 | B2 | 12/2015 | Prentice |
| 9,228,014 | B2 | 1/2016 | Classon et al. |
| 9,260,515 | B2 | 2/2016 | Stitt et al. |
| 9,265,827 | B2 | 2/2016 | Wiegand et al. |
| 9,266,949 | B2 | 2/2016 | Ramasubramanyan et al. |
| 9,302,015 | B2 | 4/2016 | Papadopoulos et al. |
| 9,353,176 | B2 | 5/2016 | MacDonald et al. |
| 9,359,434 | B2 | 6/2016 | Subramanian et al. |
| 9,402,898 | B2 | 8/2016 | Walsh et al. |
| 9,447,431 | B2 | 9/2016 | Thess et al. |
| 9,499,616 | B2 | 11/2016 | Subramanian et al. |
| 9,644,181 | B2 | 5/2017 | Matsuyama et al. |
| 9,663,810 | B2 | 5/2017 | Prentice |
| 9,714,411 | B2 | 7/2017 | Grillberger et al. |
| 9,758,568 | B2 | 9/2017 | Grillberger et al. |
| 9,809,796 | B2 | 11/2017 | Grillberger et al. |
| 10,023,892 | B2 | 7/2018 | Wong et al. |
| 10,927,342 | B2 | 2/2021 | Johnson et al. |
| 11,319,567 | B2 | 5/2022 | Wong et al. |
| 11,332,771 | B2 | 5/2022 | Oshodi et al. |
| 2005/0019859 | A1 | 1/2005 | Schilling et al. |
| 2006/0094104 | A1 | 5/2006 | Grillberger et al. |
| 2006/0094113 | A1 | 5/2006 | Epstein et al. |
| 2006/0115901 | A1 | 6/2006 | Valamehr et al. |
| 2007/0212770 | A1 | 9/2007 | Grillberger et al. |
| 2007/0212778 | A1 | 9/2007 | Bramke et al. |
| 2007/0275439 | A1 | 11/2007 | Opstelten |
| 2009/0074793 | A1 | 3/2009 | Martin et al. |
| 2009/0137416 | A1 | 5/2009 | Fandl et al. |
| 2009/0162901 | A1 | 6/2009 | Chen et al. |
| 2010/0120093 | A1 | 5/2010 | Von et al. |
| 2010/0227819 | A1 | 9/2010 | Hernandez et al. |
| 2010/0285533 | A1 | 11/2010 | Krueger et al. |
| 2010/0304436 | A1 | 12/2010 | Chen et al. |
| 2010/0331527 | A1 | 12/2010 | Davis et al. |
| 2011/0229933 | A1 | 9/2011 | Krishnan et al. |
| 2012/0034674 | A1 | 2/2012 | Grillberger et al. |
| 2012/0264170 | A1 | 10/2012 | Merchant et al. |
| 2012/0308549 | A1 | 12/2012 | Fogh et al. |
| 2013/0084605 | A1 | 4/2013 | Zhou et al. |
| 2013/0130316 | A1 | 5/2013 | Joosten et al. |
| 2013/0224855 | A1 | 8/2013 | Gupta et al. |
| 2013/0295613 | A1 | 11/2013 | Kishishita et al. |
| 2013/0344535 | A1 | 12/2013 | Mundt et al. |
| 2014/0044730 | A1 | 2/2014 | Yancopoulos et al. |
| 2014/0088295 | A1 | 3/2014 | Smith et al. |
| 2014/0154726 | A1 | 6/2014 | Yang et al. |
| 2014/0271642 | A1 | 9/2014 | Murphy et al. |
| 2014/0271653 | A1 | 9/2014 | Gurnett-Bander et al. |
| 2014/0271658 | A1 | 9/2014 | Murphy et al. |
| 2014/0271681 | A1 | 9/2014 | Martin et al. |
| 2014/0273095 | A1 | 9/2014 | Oshodi et al. |
| 2015/0203579 | A1 | 7/2015 | Papadopoulos et al. |
| 2015/0203580 | A1 | 7/2015 | Papadopoulos et al. |
| 2015/0216795 | A1 | 8/2015 | Assadourian et al. |
| 2015/0259423 | A1 | 9/2015 | Kirshner et al. |
| 2015/0266966 | A1 | 9/2015 | Smith et al. |
| 2015/0313194 | A1 | 11/2015 | Hu et al. |
| 2015/0337029 | A1 | 11/2015 | Kyratsous et al. |
| 2015/0337045 | A1 | 11/2015 | Okamoto et al. |
| 2016/0002594 | A1 | 1/2016 | Yang et al. |
| 2016/0017029 | A1 | 1/2016 | Walsh et al. |
| 2016/0024502 | A1 | 1/2016 | Streicher et al. |
| 2016/0075778 | A1 | 3/2016 | Okamoto et al. |
| 2016/0076068 | A1 | 3/2016 | Engel et al. |
| 2016/0083689 | A1 | 3/2016 | Grillberger et al. |
| 2016/0215040 | A1 | 7/2016 | Kyratsous et al. |
| 2016/0237400 | A1 | 8/2016 | Xian |
| 2016/0333385 | A1 | 11/2016 | Kang et al. |
| 2017/0107553 | A1 | 4/2017 | Kottakota et al. |
| 2017/0305999 | A1 | 10/2017 | Leber et al. |
| 2018/0223249 | A1 | 8/2018 | Johnson et al. |
| 2018/0298078 | A1 | 10/2018 | Park et al. |
| 2018/0346881 | A1 | 12/2018 | Clemens et al. |
| 2019/0010531 | A1 | 1/2019 | Chen et al. |
| 2019/0092836 | A1 | 3/2019 | Leister et al. |
| 2019/0153496 | A1 | 5/2019 | Gupta et al. |
| 2020/0131554 | A1 | 4/2020 | Chen et al. |
| 2020/0149081 | A1 | 5/2020 | Oshodi et al. |
| 2020/0157492 | A1 | 5/2020 | Johnson et al. |
| 2020/0255880 | A1 | 8/2020 | Chen et al. |
| 2021/0332402 | A1 | 10/2021 | Oshodi et al. |
| 2021/0340560 | A1 | 11/2021 | Clarke |
| 2021/0388408 | A1 | 12/2021 | Chen et al. |
| 2022/0228187 | A1 | 7/2022 | Oshodi et al. |
| 2022/0372436 | A1 | 11/2022 | Oshodi et al. |

FOREIGN PATENT DOCUMENTS

| | | | | |
|---|---|---|---|---|
| CN | 101065480 A | 10/2007 | | |
| CN | 101220347 A | 7/2008 | | |
| CN | 101360820 A | 2/2009 | | |
| CN | 101603026 A | 12/2009 | | |
| CN | 102115728 A | 7/2011 | | |
| CN | 102224239 A | 10/2011 | | |
| CN | 102317440 A | 1/2012 | | |
| CS | 271503 B1 | 10/1990 | | |
| EP | 1321515 | 6/2003 | | |
| EP | 2971040 B1 | 9/2018 | | |
| JP | 2008517610 A | 5/2008 | | |
| JP | 2013-208104 A | 10/2013 | | |
| RU | 2383616 C2 | 3/2010 | | |
| RU | 2518289 C2 | 6/2014 | | |
| WO | WO 99/035255 A2 | 7/1999 | | |
| WO | WO 00/75319 A1 | 12/2000 | | |
| WO | WO-02069733 A1 | 9/2002 | | |
| WO | WO-02101019 A2 | 12/2002 | | |
| WO | WO 2005/028626 A2 | 3/2005 | | |
| WO | WO-2006014683 A2 | 2/2006 | | |
| WO | WO 2007/077217 A2 | 7/2007 | | |
| WO | WO-2008033517 A2 | 3/2008 | | |
| WO | WO 2008/063892 A2 | 5/2008 | | |
| WO | WO-2008131374 A1 | 10/2008 | | |
| WO | WO 2008/147143 | 12/2008 | | |
| WO | WO 2008/154014 A2 | 12/2008 | | |
| WO | WO 2011/079004 A1 | 6/2011 | | |
| WO | WO 2012/091124 A1 | 7/2012 | | |
| WO | WO-2013066761 A1 | 5/2013 | | |
| WO | WO 2014/020160 A1 | 2/2014 | | |
| WO | WO-2014144198 A1 | * 9/2014 | .......... | C12N 5/0031 |
| WO | WO-2014160790 A1 | 10/2014 | | |

(56) References Cited

FOREIGN PATENT DOCUMENTS

| | | | |
|---|---|---|---|
| WO | WO 2015/105609 | A1 | 7/2015 |
| WO | WO-2015184009 | A1 | 12/2015 |
| WO | WO-2019010191 | A1 | 1/2019 |

OTHER PUBLICATIONS

Hamm M, Wang Y, Rustandi RR. Characterization of N-Linked Glycosylation in a Monoclonal Antibody Produced in NS0 Cells Using Capillary Electrophoresis with Laser-Induced Fluorescence Detection. Pharmaceuticals (Basel). Mar. 21, 2013;6(3):393-406. (Year: 2013).*

Cai, J.,"Microbiology of Grain and Oil Food", China Light Industry Press Ltd (Mar. 31, 2002); p. 83; 2 pages.

Allen et al., "Inhibition of Lymphocyte Proliferation by Polyamines Requires Ruminant-Plasma Polyamine Oxidase," Eur. J. Biochem. 102, 153-158 (1979).

Altamirano et al., "Analysis of CHO Cells Metabolic Redistribution in a Glutamate-Based Defined Medium in Continuous Culture," Biotechnol. Prog., Nov.-Dec. 2001, 17(6), pp. 1032-1041.

Ashkenazi et al., "Protection against endotoxic shock by a tumor necrosis factor receptor immunoadhesin," PNAS USA, Dec. 1991, 88:10535-10539.

Bettger et al., "Rapid clonal growth and serial passage of human diploid fibroblasts in a lipid-enriched synthetic medium supplemented with epidermal growth factor, insulin, and dexamethasone," Proc. Natl. Acad. Sci. USA, 1981, 78(9), pp. 5588-5592.

Bokati et al., "Corrosion inhibition of copper, mild steel and galvanically coupled coppermild steel in artificial sea water in presence of 1H-benzotriazole, sodium molybdate and sodium phosphate," Corrosion Science (2017) 126:272-285.

Branca et al., "Inhibition of Ornithine Decarboxylase of Hela Cells by Diamines and Polyamines," Biochem. J. (1980) 186, 925-931.

Brasel et al., "Hematologic Effects of flt3 Ligand In Vivo in Mice," Blood, 1996, 88(6), pp. 2004-2012.

Byrn et al., "Biological properties of a CD4 immunoadhesin," Nature (1990) 344:667-670.

Davidson et al., "The Nucleoprotein Content of Fibroblasts Growing in vitro," Biochem. J., 1945, 39(2), pp. 188-199.

Dulbecco et al., "Production of Plaques in Monolayer Tissue Cultures by Single Particulars of an Animal Virus," Proc. Natl. Acad. Sci. USA, 1952, 38(8), pp. 747-752.

Eagle et al., "Nutrition Needs of Mammalian Cells in Tissue Culture," Science, 1955, 122(3168), pp. 501-504.

Extended European Search Report for European Application No. 18172141.6, mailed Jun. 29, 2018, 11 pages.

Franěk et al., "Plant Protein Hydrolysates: Preparation of Defined Peptide Fractions Promoting Growth and Production in Animal Cells Cultures," Biotechnol. Prog. 16 (5):688-92 (2000).

Froud et al., "Polyamine enhanced product expression from transformed and recombinant cell lines,"Production of Biologicals from Animal Cells in Culture (Editors: Spier et al.), Butterworth-Heinemann Ltd, Oxford, 1991, pp. 107-109.

Fusi et al., "Effects of putrescine, cadaverine, spermine, spermidine, and β-phenylethylamine on cultured bovine mammary epithelial cells," Ital. J. Anim. Sci., vol. 7, 131-140, 2008.

Gahl et al., "Reversal by aminoguanidine of the inhibition of proliferation of human fibroblasts by spermidine and spermine," Chem.—Biol Interactions, 22 (1978) 91-98.

Google® Scholar search, "a trap molecule" pp. 1-2; Jul. 23, 2020.

Guirard et al., "Effect of polyamine structure on growth stimulation and spermine and spermidine content of lactic acid bacteria," Journal of Bacteriology, vol. 88, No. 1, p. 72-80, Jul. 1964.

Ham, "Clonal Growth of Mammalian Cells in a Chemically Defined, Synthetic Medium," Nat'l Acad. Sci. USA, 1965, 53, pp. 288-293.

Han et al., "Effects of polyamines on apoptosis induced by simulated ischemia/reperfusion injury in cultured neonatal rat cardiomyocytes," Cell Biology International 31 (2007) 1345-1352.

Hawel, L. et al., "Selective putrescine export is regulated by insulin and ornithine in Reuber H35 hepatoma cells," Biochimica et Biophysica Acta, vol. 1222, No. 1, pp. 15-26, May 1994.

Hollenbaugh et al., "Construction of Immunoglobulin Fusion Proteins," Current Protocols in Immunology (2002), Supplement 48, Unit 10.19A, pp. 10.19A.1-10.19A.11.

Holliger et al., "Diabodies: small bivalent and bispecific antibody fragments," PNAS USA, Jul. 1993, 90:6444-6448.

Holmes et al., "Serum Fractionation and the Effects of Bovine Serum Fractions on Human Cells Grown in a Chemically Defined Medium," Biochem. Cytol., 1961, 10, pp. 389-401.

Holtta, E. et al., "Polyamine dependence of Chinese hamster ovary cells in serum-free culture is due to deficient arginase activity," Biochimica et Biophysica Acta, vol. 721, No. 4, pp. 321-327, Dec. 1982.

Huang et al., "Maximizing Productivity of CHO Cell-Based Fed-Batch Culture Using Chemically Defined Media Conditions and Typical Manufacturing Equipment," Biotechnol. Prog., Sep.-Oct. 2010, 26(5), pp. 1400-1410.

Igarashi, K. et al, "Modulation of cellular function by polyamines," International Journal of Biochemistry and Cell Biology, vol. 42, No. 1, pp. 39-51, Jan. 2010.

International Search Report and Written Opinion of the International Search Authority for International Application No. PCT/US18/40734, mailed Oct. 18, 2018, 18 pages.

Jensen et al., "Selective inhibition of fibroblasts by spermine in primary cultures of normal human skin epithelial cells," In Vitro, vol. 18, No. 10, Oct. 1982, pp. 867-871.

Kanemura et al., "In Vitro Screening of Exogenous Factors for Human Neural Stem/Progenitor CellProliferation Using Measurement of Total ATP Content in Viable Cells," Cell Transplantation, 2005, vol. 14, pp. 673-682.

Kang et al., "Metabolic markers associated with high mannose glycan levels of therapeutic recombinant monoclonal antibodies," Journal of Biotechnology (2015) 203: 22-31.

Kaufman, "Use of Recombinant DNA Technology for Engineering Mammalian Cells to Produce Proteins," Bioprocess Technology, 1990, vol. 10, pp. 15-69.

Kaufman et al., "Synthesis, Processing, and Secretion of Recombinant Human Factor VIII Expressed in Mammalian Cells," J. Biol. Chem., 1988, 263(13), pp. 6352-6362.

Kaufman, "Selection and Coamplification of Heterologous Genes in Mammalian Cells," Meth Enzymol, 1990, 185, pp. 537-566.

Kipriyanov et al., "Recombinant single-chain Fv fragments carrying C-terminal cysteine residues: Production of bivalent and biotinylated miniantibodies," Mol. Immunol. (1994) 31:1047-1058.

Kipriyanov et al., "Single-chain antibody streptavidin fusions: tetrameric bifunctional scFv-complexes with biotin binding activity and enhanced affinity to antigen," Human Antibodies and Hybridomas (1995) 6:93-101.

Li and Wen, "Screening soy hydrolysates for the production of a recombinant therapeutic protein in commercial cell line by combined approach of near-infrared spectroscopy and chemometrics," Appl Microbiol Biotechnol (2013) 97:2653-2660.

McKinnon et al., "Expression, purification and characterization of secreted recombinant humaninsulin-like growth factor I (IGF-1) and the potent variant des (1-3) IGF-1 in Chinese hamster ovary cells," J. Mol. Endocrinol., 1991, 6, pp. 231-239.

Michael, A.J., "Biosynthesis of polyamines and polyamine containing molecules," Biochem. J. (2016) 473, 2315-2329.

Moore and Stein, "A Modified Ninhydrin Reagent for the Photometric Determination of Amino Acids and Related Compounds," J. Biol. Chem. 1954, vol. 211, pp. 907-913.

Moore et al., "Culture of Normal Human Leukocytes," J. Amer. Med. Assoc., 1967, 199(8), pp. 519-524.

Morrison and Seidel, "Cell spreading and the regulation of ornithine decarboxylase," Journal of Cell Science (1995) 108: 3787-3794.

Nagae et al., "Function and 3D Structure of the N-Glycans on Glycoproteins," Int. J Mol. Sci. 2012, 13, 8398-8429.

Nemkov et al., "Three-minute method for amino acid analysis by UHPLC and high-resolution quadrupole orbitrap mass spectrometry," Amino Acids, 2015, 47(11):2345-2357, 23 pages provided.

(56) References Cited

OTHER PUBLICATIONS

Ornithine, Wikipedia, 3 pages, retrieved from https://en.wikipedia.org/wiki/Ornithine on May 11, 2020.
Orr et al., "Survival of Animal Tissue Cells in Primary Culture in the Absence of Serum," Appl. Microbiol., 1973, 25(1), pp. 49-54.
Pastorian et al., "Tolerance to Putrescine Toxicity in Chinese Hamster Ovary Cells Is Associated with Altered Uptake and Export," Experimental Cell Research, 231, 284-295 (1997).
Pegg, "Regulation of Ornithine Decarboxylase," J. of Biol. Chem., May 2006, 281:21, pp. 14529-14532.
Pegg, "Toxicity of Polyamines and Their Metabolic Products," Chemical Research in Toxicology, 2013, 26, 1782-1800.
Poljak, RJ, "Production and structure of diabodies," Structure, Dec. 1994, 2:1121-1123.
Putrescine, Wikipedia, 5 pages, retrieved from https://en.wikipedia.org/wiki/Putrescine on May 11, 2020.
Richardson et al., "Metabolomics Analysis of Soy Hydrolysates for the Identification of ProductivityMarkers of Mammalia Cells for Manufacturing Therapeutic Proteins," Biotechnol. Prog., 2015, 31:522-531.
Rodrigues et al., "Comparison of commercial serum-free media for CHO-K1 cell growth and monoclonal antibody production," International Journal of Pharmaceutics (2012) 437: 303-305.
Rohrer et al., "Profiling N-linked oligosaccharides from IgG by high-performance anion-exchange chromatography with pulsed amperometric detection," Glycobiology, 2016, vol. 26, No. 6, 582-591.
Sarilumab, Wikipedia, 3 pages, downloaded May 25, 2020, retrieved from https://en.wikipedia.org/wiki/Sarilumab.
Shantz and Levin, "Regulation of ornithine decarboxylase during oncogenic transformation: mechanisms and therapeutic potential," Amino Acids (2007) 33: 213-223.
Sigma-Aldrich, "Ethylenediaminetetraacetic acid tetrasodiurn salt dihydrate," downloaded May 26, 2020, 3 pages, retrieved from https://www.sigmaaldrich.com/catalog/product/sigma/e6511?lang=en&region=US.
Sigma-Aldrich, "Nutrient Mixture F-12 Ham Formulation," Jan. 18, 2009, 7 pages, retrievedfrom https://www.sigmaaldrich.com/life-science/cell-culture/learning-center/media-formulations/f-12-ham.html on Apr. 12, 2019.
Stoner et al., "Putrescine stimulates growth of human bronchial epithelial cells in primary culture," In Vitro, 1980, 16(5):399-406.
Taylor et al., "A transgenic mouse that expresses a diversity of human sequence heavy and light chain immunoglobulins," Nucl. Acids Res., (1992) 20(23):6287-6295.
Declerck and Tebbey, "Importance of manufacturing consistency of the glycosylated monoclonal antibody adalimumab (Humira®) and potential impact on the clinical use of biosimilars," Generics and Biosimilars Initiative Journal (2016) 5:2, pp. 70-73.
ThermoFisher Scientific, Technical Resources, 11320, DMEM/F-12, [online], Retrieved from the|Internet: <URL: http://www.thermofisher.com/US/en/home/technical-resources/media-formulation.55.html>, Retrieved from the Internet on Jan. 29, 2018, 3 pages.
Tobias et al., "Exposure to Ornithine Results in Excessive Accumulation of Putrescine and Apoptotic Cell Death in Ornithine Decarboxylase Overproducing Mouse Myeloma Cells," Cell Growth & Differentiation, Oct. 1995, vol. 6, 1279-1285.
Tome et al., "Excess putrescine accumulation inhibits the formation of modified eukaryotic initiation factor 5A (eIF-5A) and induces apoptosis," Biochem. J., (1997) 328, 847-854.
Urlaub et al., "Isolation of Chinese hamster cell mutants deficient in dihydrofolate reductase activity," Proc. Natl. Acad. Sci. USA, 1980, 77(7), pp. 4216-4220.
Wahl and Holzgrabe, "Amino acid analysis for pharmacopoeial purposes," Talanta, Jul. 2016, 154:150-163.
Ward et al., "Binding activities of a repertoire of single immunoglobulin variable domains secreted from *Escherichia coli*," Nature (1989) 341:544-546.
Williams et al., "Isolation and Long-Term Cell Culture of Epithelial-Like Cells From Rat Liver," Exp. Cell. Res., 1971, 69, pp. 106-112.
Wood et al., "High Level Synthesis of Immunoglobulins in Chinese Hamster Ovary Cells," J. Immuno., 1990, 145(9), pp. 3011-3016.
Casero, Jr. and Marton, "Targeting polyamine metabolism and function in cancer and other hyperproliferative diseases," Nature Reviews Drug Discovery, May 2007, vol. 6, pp. 373-390.
Experimental report—Impact of Ornithine and Putrescine Addition on MB02 Culture, submitted by the opponent on Jul. 16, 2020 in Opposition Against European Patent No. 2970876, 9 pages.
Extract from Mosby's Medical Dictionary, 8th Edition, 2009 :1161-1162.
Gupta, A.J., "Correlating composition and functionality of soy protein hydrolysates used in animal cell cultures," PhD thesis, Wageningen University, NL (2015), ISBN: 978-94-6257-320-8, pp. 1-127.
Kou et al., "Increasing the productivity of TNFR-Fc in GS-CHO cells at reduced culture temperatures," Biotechnology and Bioprocess Engineering, 2011, vol. 16, pp. 136-143.
Kumar et al., "Differential protein expression following low temperature culture of suspension CHO-K1 cells," BMC Biotechnology, 2008, 8:42, 13 pages.
Kucharzewska et al., "Ornithine decarboxylase and extracellular polyamines regulate microvascular sprouting and actin cytoskeleton dynamics in endothelial cells," Experimental Cell Research (2010) 316: 2683-2691.
Lalonde et al., "Therapeutic glycoprotein production in mammalian cells," Journal of Biotechnology 251 (2017) 128-140.
Matsuoka et al., "Improvement of production rate on recombinant CHO cells in two-stage culture," BMC Proceedings, 2013, 7(Suppl 6):P50, 2 pages.
Oguchi et al., "pH Condition in temperature shift cultivation enhances cell longevity and specific hMab productivity in CHO culture," Cytotechnology, 2006, 52: 199-207.
Purwaha et al., "Targeted metabolomic analysis of amino acid response to L-asparaginase in adherent cells," Metabolomics (2014) 10:909-919.
Raafay et al., "Aflibercept: a Potent Vascular Endothelial Growth Factor Antagonist for Neovascular Age-Related Macular Degeneration and Other Retinal Vascular Diseases," Biol Ther, 2012, 2:3, 22 pages.
Rasmussen et al., "Isolation, characterization and recombinant protein expression in Veggie-CHO: a serum-free CHO host cell line," Cytotechnology, 1998, 28: 31-42.
Ritacco et al., "Cell Culture Media for Recombinant Protein Expression in Chinese Hamster Ovary (CHO) Cells: History, Key Components, and Optimization Strategies," Biotechnol Prog., 2018, vol. 34, No. 6, pp. 1407-1426.
Shi et al., "A High-throughput Automated Platform for the Development of Manufacturing Cell Lines for Protein Therapeutics," Journal of Visualized Experiments, Sep. 2011, 55, e3010, 5 pages.
Anumula, K. R., et al., "High Resolution and High Sensitivity Methods for Oligosaccharide Mapping and Characterization by Normal Phase High Performance Liquid Chromatography Following Derivatization With Highly Fluorescent Anthranilic Acid", Glycobiology (1998); 8(7): 685-694.
Borys, M. C., et al., "Effects of culture conditions on N-glycolylneuraminic acid (Neu5Gc) content of a recombinant fusion protein produced in CHO cells", Biotechnology and Bioengineering (2010); 105(6): 1048-1057.
Largy, E., et al., "Orthogonal liquid chromatography-mass spectrometry methods for the comprehensive characterization of therapeutic glycoproteins, from released glycans to intact protein level", Journal of Chromatography A (2017); 1498: 128-146.
Wu, W., et al., "Biochemistry", China Medical Science Press (Aug. 31, 2015); Section 2: pp. 120-121; 10 pages with English translation.

* cited by examiner

FIG. 6B

| Condition | Control | Low Orn. Spike | High Orn. Spike | Putrescine Spike |
|---|---|---|---|---|
| Conc., mg/L | 1.6 | 6.6 | 31.6 | 36.6 |
| Titer, g/L | 1.61 | 1.55 | 1.55 | 1.63 |
| IVCD, x$10^6$ cells-day/ml | 80.9 | 110.4 | 96.2 | 104.8 |
| Peak 11, % | 12.5 | 9.8 | 9.3 | 9.0 |

```
                         SEQUENCE LISTING


<160> NUMBER OF SEQ ID NOS: 2

<210> SEQ ID NO 1
<211> LENGTH: 879
<212> TYPE: PRT
<213> ORGANISM: Artificial
<220> FEATURE:
<223> OTHER INFORMATION: synthetic

<400> SEQUENCE: 1

Ser Glu Arg Cys Asp Asp Trp Gly Leu Asp Thr Met Arg Gln Ile Gln
1               5                   10                  15

Val Phe Glu Asp Glu Pro Ala Arg Ile Lys Cys Pro Leu Phe Glu His
            20                  25                  30

Phe Leu Lys Phe Asn Tyr Ser Thr Ala His Ser Ala Gly Leu Thr Leu
        35                  40                  45

Ile Trp Tyr Trp Thr Arg Gln Asp Arg Asp Leu Glu Glu Pro Ile Asn
    50                  55                  60

Phe Arg Leu Pro Glu Asn Arg Ile Ser Lys Glu Lys Asp Val Leu Trp
65                  70                  75                  80
```

-continued

```
Phe Arg Pro Thr Leu Leu Asn Asp Thr Gly Asn Tyr Thr Cys Met Leu
                85                  90                  95

Arg Asn Thr Thr Tyr Cys Ser Lys Val Ala Phe Pro Leu Glu Val Val
            100                 105                 110

Gln Lys Asp Ser Cys Phe Asn Ser Pro Met Lys Leu Pro Val His Lys
        115                 120                 125

Leu Tyr Ile Glu Tyr Gly Ile Gln Arg Ile Thr Cys Pro Asn Val Asp
    130                 135                 140

Gly Tyr Phe Pro Ser Ser Val Lys Pro Thr Ile Thr Trp Tyr Met Gly
145                 150                 155                 160

Cys Tyr Lys Ile Gln Asn Phe Asn Asn Val Ile Pro Glu Gly Met Asn
                165                 170                 175

Leu Ser Phe Leu Ile Ala Leu Ile Ser Asn Asn Gly Asn Tyr Thr Cys
            180                 185                 190

Val Val Thr Tyr Pro Glu Asn Gly Arg Thr Phe His Leu Thr Arg Thr
        195                 200                 205

Leu Thr Val Lys Val Val Gly Ser Pro Lys Asn Ala Val Pro Pro Val
    210                 215                 220

Ile His Ser Pro Asn Asp His Val Val Tyr Glu Lys Glu Pro Gly Glu
225                 230                 235                 240

Glu Leu Leu Ile Pro Cys Thr Val Tyr Phe Ser Phe Leu Met Asp Ser
                245                 250                 255

Arg Asn Glu Val Trp Trp Thr Ile Asp Gly Lys Lys Pro Asp Asp Ile
            260                 265                 270

Thr Ile Asp Val Thr Ile Asn Glu Ser Ile Ser His Ser Arg Thr Glu
        275                 280                 285

Asp Glu Thr Arg Thr Gln Ile Leu Ser Ile Lys Lys Val Thr Ser Glu
    290                 295                 300

Asp Leu Lys Arg Ser Tyr Val Cys His Ala Arg Ser Ala Lys Gly Glu
305                 310                 315                 320

Val Ala Lys Ala Ala Lys Val Lys Gln Lys Val Pro Ala Pro Arg Tyr
                325                 330                 335

Thr Val Glu Lys Cys Lys Glu Arg Glu Glu Lys Ile Ile Leu Val Ser
            340                 345                 350

Ser Ala Asn Glu Ile Asp Val Arg Pro Cys Pro Leu Asn Pro Asn Glu
        355                 360                 365

His Lys Gly Thr Ile Thr Trp Tyr Lys Asp Asp Ser Lys Thr Pro Val
    370                 375                 380

Ser Thr Glu Gln Ala Ser Arg Ile His Gln His Lys Glu Lys Leu Trp
385                 390                 395                 400

Phe Val Pro Ala Lys Val Glu Asp Ser Gly His Tyr Tyr Cys Val Val
                405                 410                 415

Arg Asn Ser Ser Tyr Cys Leu Arg Ile Lys Ile Ser Ala Lys Phe Val
            420                 425                 430

Glu Asn Glu Pro Asn Leu Cys Tyr Asn Ala Gln Ala Ile Phe Lys Gln
        435                 440                 445

Lys Leu Pro Val Ala Gly Asp Gly Gly Leu Val Cys Pro Tyr Met Glu
    450                 455                 460

Phe Phe Lys Asn Glu Asn Asn Glu Leu Pro Lys Leu Gln Trp Tyr Lys
465                 470                 475                 480

Asp Cys Lys Pro Leu Leu Leu Asp Asn Ile His Phe Ser Gly Val Lys
                485                 490                 495

Asp Arg Leu Ile Val Met Asn Val Ala Glu Lys His Arg Gly Asn Tyr
```

-continued

```
            500                 505                 510

Thr Cys His Ala Ser Tyr Thr Tyr Leu Gly Lys Gln Tyr Pro Ile Thr
        515                 520                 525

Arg Val Ile Glu Phe Ile Thr Leu Glu Glu Asn Lys Pro Thr Arg Pro
    530                 535                 540

Val Ile Val Ser Pro Ala Asn Glu Thr Met Glu Val Asp Leu Gly Ser
545                 550                 555                 560

Gln Ile Gln Leu Ile Cys Asn Val Thr Gly Gln Leu Ser Asp Ile Ala
                565                 570                 575

Tyr Trp Lys Trp Asn Gly Ser Val Ile Asp Glu Asp Asp Pro Val Leu
            580                 585                 590

Gly Glu Asp Tyr Tyr Ser Val Glu Asn Pro Ala Asn Lys Arg Arg Ser
        595                 600                 605

Thr Leu Ile Thr Val Leu Asn Ile Ser Glu Ile Glu Ser Arg Phe Tyr
    610                 615                 620

Lys His Pro Phe Thr Cys Phe Ala Lys Asn Thr His Gly Ile Asp Ala
625                 630                 635                 640

Ala Tyr Ile Gln Leu Ile Tyr Pro Val Thr Asn Ser Gly Asp Lys Thr
                645                 650                 655

His Thr Cys Pro Pro Cys Pro Ala Pro Glu Leu Leu Gly Gly Pro Ser
            660                 665                 670

Val Phe Leu Phe Pro Pro Lys Pro Lys Asp Thr Leu Met Ile Ser Arg
        675                 680                 685

Thr Pro Glu Val Thr Cys Val Val Val Asp Val Ser His Glu Asp Pro
    690                 695                 700

Glu Val Lys Phe Asn Trp Tyr Val Asp Gly Val Glu Val His Asn Ala
705                 710                 715                 720

Lys Thr Lys Pro Arg Glu Glu Gln Tyr Asn Ser Thr Tyr Arg Val Val
                725                 730                 735

Ser Val Leu Thr Val Leu His Gln Asp Trp Leu Asn Gly Lys Glu Tyr
            740                 745                 750

Lys Cys Lys Val Ser Asn Lys Ala Leu Pro Ala Pro Ile Glu Lys Thr
        755                 760                 765

Ile Ser Lys Ala Lys Gly Gln Pro Arg Glu Pro Gln Val Tyr Thr Leu
    770                 775                 780

Pro Pro Ser Arg Asp Glu Leu Thr Lys Asn Gln Val Ser Leu Thr Cys
785                 790                 795                 800

Leu Val Lys Gly Phe Tyr Pro Ser Asp Ile Ala Val Glu Trp Glu Ser
                805                 810                 815

Asn Gly Gln Pro Glu Asn Asn Tyr Lys Thr Thr Pro Pro Val Leu Asp
            820                 825                 830

Ser Asp Gly Ser Phe Phe Leu Tyr Ser Lys Leu Thr Val Asp Lys Ser
        835                 840                 845

Arg Trp Gln Gln Gly Asn Val Phe Ser Cys Ser Val Met His Glu Ala
    850                 855                 860

Leu His Asn His Tyr Thr Gln Lys Ser Leu Ser Leu Ser Pro Gly
865                 870                 875
```

<210> SEQ ID NO 2
<211> LENGTH: 431
<212> TYPE: PRT
<213> ORGANISM: Artificial
<220> FEATURE:
<223> OTHER INFORMATION: synthetic

```
<400> SEQUENCE: 2

Ser Asp Thr Gly Pro Arg Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
    370                 375                 380

Ser Asp Gly Ser Phe Phe Leu Tyr Ser Lys Leu Thr Val Asp Lys Ser
385                 390                 395                 400
```

-continued

```
Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly
            420                 425                 430
```

CELL CULTURE PROCESS FOR MAKING A GLYCOPROTEIN

CROSS-REFERENCE TO RELATED APPLICATIONS

This application is a division of U.S. patent application Ser. No. 16/026,539, filed Jul. 3, 2018, which claims priority to and the benefit of U.S. Provisional Patent Application Ser. Nos. 62/529,471, filed Jul. 6, 2017, and 62/625,744 filed Feb. 2, 2018, the contents of each of which are herein incorporated by reference in their entireties.

INCORPORATION OF THE SEQUENCE LISTING

The contents of the text filed named "REGE009D01US_SeqList.txt", which was created on Aug. 23, 2021 and is 11.3 KB in size, are hereby incorporated by reference in their entirety.

FIELD

The invention relates to methods for the culturing of cells and for the production of recombinant proteins. The invention specifically relates to methods for the culturing of cells in soy hydrolysate-containing media to achieve consistent production of high quality recombinant protein.

BACKGROUND

Cell culture media containing protein hydrolysates, such as soy hydrolysate, are commonly used in the production of recombinant proteins from cultured cells. However, protein hydrolysates may contain compounds that negatively impact cell growth or recombinant protein production. Despite these drawbacks, protein hydrolysates have been widely used as supplements in cell culture.

Human biological therapeutics (biopharmaceuticals) are generally produced in mammalian cell culture. However, the quality and performance of biological therapeutics are highly dependent upon the manufacturing process. Tebbey, P. and Declerck, P. Generics and Biosimilars Initiative Journal (2016) 5:2, pp. 70-73 is incorporated herein for manufacturing biological drugs with consistent glycosylation. Changes to the cell culture process for the manufacture of glycoproteins may lead to variation in glycosylation pattern, the presence of acidic species (e.g., sialic acid) or the amount of glycan on a protein. Id. Such variation increases heterogeneity of protein isoforms in the resulting protein production, which can alter stability, efficacy or immunogenicity of the biological therapeutic and ultimately lead to the rejection of the lot of proteins.

Hence, cell culture methods that eliminate lot-to-lot variability in drug product yield and composition are highly desirable. The present disclosure identifies certain components in plant protein hydrolysate (e.g., soy hydrolysate) that can vary from batch-to-batch and alter the composition and yield of high quality glycoproteins produced in culture using soy hydrolysate. The present disclosure addresses the need for improved cell culture methods by, among other things, screening batches of plant protein hydrolysate and selecting those batches that include a desirable concentration of a component of plant protein hydrolysate for use in the production of biopharmaceuticals.

SUMMARY

The present disclosure is predicated in part on the discovery that the concentration of ornithine or putrescine in a batch of soy hydrolysate affects the quality and composition of proteins produced in cell culture using soy hydrolysate. The present disclosure also provides that cells cultured in media including soy hydrolysate comprising certain concentrations of ornithine or putrescine produce greater amounts of high quality proteins exhibiting more consistent glycosylation patterns, amounts of glycan and sialic acid profiles from lot-to-lot.

In one aspect, the invention relates to a method of culturing a population of cells expressing a recombinant heterologous glycoprotein in cell culture media comprising soy hydrolysate to produce the recombinant heterologous glycoprotein, and wherein the soy hydrolysate comprises ≤0.067% (w/w) ornithine or putrescine.

In some embodiments, the method includes the steps of culturing a population of cells expressing a recombinant heterologous glycoprotein in cell culture media comprising soy hydrolysate containing ≤less than 0.67 milligram (mg) of ornithine per gram (g) of soy (w/w), or about 0.003%-0.067% (w/w) ornithine. In one embodiment, the culture media contains ≤5 mg/L ornithine, or about 0.6-3 mg/L ornithine. In some embodiments, the population of cells is obtained by clonal expansion of a cell expressing a recombinant heterologous glycoprotein.

In one aspect, the invention relates to a method for producing a glycoprotein. In one embodiment, the method includes the steps of culturing a population of cells expressing a recombinant heterologous glycoprotein in culture media containing soy hydrolysate containing ≤less than 0.67 milligram (mg) of putrescine per gram (g) of soy (w/w), or about 0.003%-0.067% (w/w) putrescine. In one embodiment, the culture media contains ≤5 mg/L putrescine, or about 0.6-3 mg/L putrescine. In some embodiments, the population of cells is obtained by clonal expansion of a cell expressing a recombinant heterologous glycoprotein.

In one embodiment, the glycoprotein is a trap molecule, such as rilonacept (IL1-trap, disclosed, e.g., in U.S. Pat. No. 6,927,004), aflibercept (VEGF-trap, disclosed, e.g., in U.S. Pat. No. 7,087,411), conbercept (VEGF-trap, disclosed, e.g., in U.S. Pat. Nos. 7,750,138 and 8,216,575), and etanercept (TNF-trap, disclosed, e.g., in U.S. Pat. No. 5,610,279.) In one embodiment, ≥10% (w/w) of the total amount of all N-glycan species of the glycoprotein is an A1 N-glycan.

In one aspect, the invention relates to a method of producing a glycoprotein. In another aspect, the invention relates to a method of using a soy hydrolysate in the producing of a glycoprotein. In another aspect, the invention relates to a method of selecting a soy hydrolysate for use in producing a glycoprotein by evaluating the quality of the produced glycoprotein. In one embodiment, the method comprises culturing a cell expressing a glycosylated protein in a cell culture media to produce the glycoprotein, purifying the glycosylated protein, subjecting the purified glycosylated protein to oligosaccharide fingerprint analysis, determining the relative amount of an A1 N-glycan compared to total amount of N-glycan species of the glycoprotein; and selecting a soy hydrolysate that provides for at least 10% (w/w) A1 N-glycan compared to total amount of N-glycan species of the glycoprotein.

In one embodiment, the method includes the steps of preparing a cell culture media containing a soy hydrolysate, culturing a cell that expresses the glycoprotein in the cell culture media, purifying the glycosylated protein, subjecting the purified glycosylated protein to oligosaccharide fingerprint analysis, determining the relative amount of an A1 N-glycan compared to total amount of N-glycan species of the glycoprotein, and then selecting the soy hydrolysate that provides for the production of a glycoprotein with at least 10% (w/w) A1 N-glycan compared to total amount of N-glycan species of the glycoprotein.

In one embodiment, the selected soy hydrolysate contains ≤0.67 mg ornithine per g soy (w/w), or about 0.003%-0.067% (w/w) ornithine. In one embodiment, the culture media contains ≤5 mg/L ornithine, or about 0.6-3 mg/L ornithine.

In one embodiment, the selected soy hydrolysate contains ≤0.67 mg putrescine per g soy (w/w), or about 0.003%-0.067% (w/w) putrescine. In one embodiment, the culture media contains ≤5 mg/L putrescine, or about 0.6-3 mg/L putrescine.

In one aspect, the invention relates to a method of selecting a soy hydrolysate for use in producing a glycoprotein by measuring the amount of ornithine or putrescine in the soy hydrolysate. In one embodiment, the method includes the steps of measuring the amount of ornithine in a soy hydrolysate, selecting a soy hydrolysate with ≤0.67 mg ornithine per g soy, or about 0.003%-0.067% (w/w) ornithine, and combining the selected soy hydrolysate with an additional ingredient to form a cell culture media with ≤5 mg/L ornithine, or about 0.6-3 mg/L ornithine. In one embodiment, the method includes the steps of measuring the amount of putrescine in a potentially useful soy hydrolysate, selecting a soy hydrolysate with ≤0.67 mg putrescine per g soy, or about 0.003%-0.067% (w/w) putrescine, and combining the selected soy hydrolysate with an additional ingredient to form a cell culture media with ≤5 mg/L putrescine, or about 0.6-3 mg/L putrescine.

In one aspect, the invention relates to a glycoprotein comprising an A1 N-glycan and at least one other N-glycan species in which the relative amount of the A1 N-glycan is at least 10% (w/w) of the total amount of N-glycans of the glycoprotein is provided. In one embodiment, the relative amount of the A1 N-glycan is about 10%-17% (w/w).

In one embodiment, the glycoprotein also has an A2 N-glycan, an A2F N-glycan, an AIF N-glycan, an NGA2F N-glycan, an NA2GIF N-glycan, an NA2 N-glycan, and an NA2F N-glycan.

In one embodiment, the glycoprotein contains 8-65 moles of sialic acid per mole of glycoprotein. In one embodiment in which the glycoprotein is rilonacept, any one of asparagine residues N37, N98, N418, and N511 of SEQ ID NO: 1 contains an A1 N-glycan. In one embodiment in which the glycoprotein is aflibercept, any one of asparagine residues N123 and N196 of SEQ ID NO: 2 contains an A1 N-glycan.

In one embodiment, the relative amount of the A1 N-glycan of the glycoprotein is determined by comparing the area under the peak of the A1 N-glycan to the total areas under the peak for all N-glycans obtained from an oligosaccharide fingerprint of the glycoprotein obtained by capillary electrophoresis.

In one aspect, a method of manufacturing soy hydrolysate having a reduced amount of ornithine or putrescine is provided. In one embodiment, the method comprises the steps of enzymatically digesting soy extract in a residue-free reaction vessel, measuring the amount of ornithine in the soy hydrolysate, and selecting those lots of soy hydrolysate containing ≤0.067% (w/w) ornithine or putrescine for use in a cell culture media. In one embodiment, the method comprises the steps of enzymatically digesting soy extract in a residue-free reaction vessel, measuring the amount of putrescine in the soy hydrolysate, and selecting soy hydrolysate with ≤0.067% (w/w) ornithine or putrescine for use in a cell culture media.

The term "about" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed disclosure. In the case of conflict, the present Specification, including definitions, will control. In addition, the materials, methods, and examples are illustrative only and are not intended to be limiting. Other features and advantages of the disclosure will be apparent from the following detailed description and claims.

BRIEF DESCRIPTION OF THE DRAWINGS

Any of the above aspects and embodiments can be combined with any other aspect or embodiment as disclosed here in the Summary and/or Detailed Description sections.

Various objects and advantages and a more complete understanding of the present invention are apparent and more readily appreciated by reference to the following Detailed Description and to the appended claims when taken in conjunction with the accompanying Drawing wherein:

FIG. 6B is a table providing the experimental conditions of each study group depicted in FIG. 6A.

DETAILED DESCRIPTION

Figure 1:
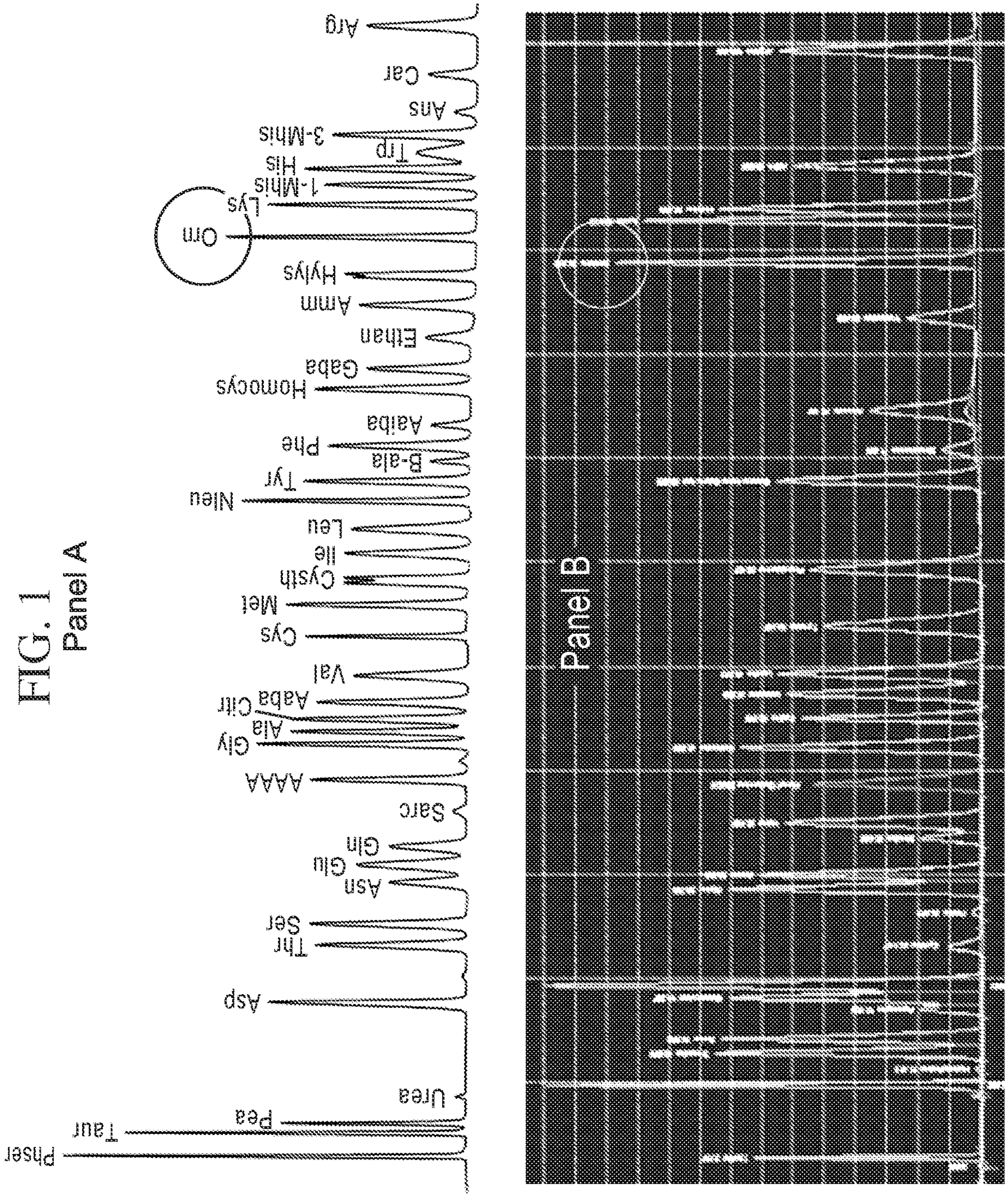
FIG. 1 depicts a chromatographic elution profile of ninhydrin-derived amino acids. The X-axis depicts time of elution from a chromatography column (retention time), and the Y-axis depicts light absorbance at 570 nm. Panel A depicts batch that does not meet the criteria for producing an acceptable N-glycan mixture by FDA standards. Panel B depicts an acceptable amino acid analysis of soy protein hydrolysate. The peak representing ornithine is circled in both chromatograms.

It is to be understood that the scope of the present disclosure is not limited to the particular methods and experimental conditions described, as such methods and conditions may vary. It is also to be understood that the terminology used herein is for the purpose of describing particular embodiments only, and is not intended to be limiting.

Unless defined otherwise, all technical and scientific terms used in this application have the same meaning as commonly understood by one of ordinary skill in the art to which this invention belongs. Although any methods and materials similar or equivalent to those described in this application can be used in the practice or testing of the present invention, certain specific methods and materials are now described. Units, prefixes, and symbols may be denoted in their standard, industry accepted form. Numeric ranges recited herein are open-bracketed, meaning that they include the numbers defining the range. Unless otherwise noted, the terms "a" or "an" are to be construed as meaning "at least one of".

The section headings used herein are for organizational purposes only and are not to be construed as limiting the subject matter described. The methods and techniques described herein are generally performed according to conventional methods known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), Harlow and Lane Antibodies: A Laboratory Manual, Cold Spring Harbor Laboratory Press, Cold Spring Harbor, N.Y. (1990), and Julio E. Celis, Cell Biology: A Laboratory Handbook, 2nd ed., Academic Press, New York, N.Y. (1998), and Dieffenbach and Dveksler, PCR Primer: A Laboratory Manual, Cold Spring Harbor Laboratory Press, Cold Spring Harbor, N.Y. (1995). All publications mentioned throughout this disclosure are incorporated herein by reference in their entirety.

Definitions

Unless defined otherwise, all technical and scientific terms used in this application have the same meaning as commonly understood by one of ordinary skill in the art to which this invention belongs.

The phrase "relative amount" means the amount of a molecular species over the total amount of all molecular species of a general type. For example, the relative amount of an A1 glycan (i.e., (GlcNAc)2(Man)3(GlcNAc)2(Gal)2 (SA)1) is calculated as amount of A1/sum of the amount of all N glycans. The relative amount can be expresses as absolute mass-to-mass amounts (i.e. gram per gram) or a percentage i.e., % (w/w).

"Ornithine" is a non-protein coding amino acid involved in the urea cycle, polyamine synthesis and arginine metabolism. Ornithine is also known to influence glycoform content of recombinant proteins. See PCT/US2014/069378. Ornithine is acted on by several enzymes. For example, ornithine decarboxylase catalyzes the conversion of ornithine to putrescine in the polyamine biosynthetic pathway. See Pegg A, J. of Biol. Chem. (2006) 281:21 pp. 14532. Additionally, ornithine conversion to citrulline is catalyzed by ornithine transcarbamylase as part of the urea cycle. Ornithine metabolism occurs in both cytosol and mitochondria of cells in culture. The presence of putrescine or presence of ornithine has been deemed critical for growth and productivity of cells cultured in chemically defined media, however the impact on critical quality attributes of a protein produced by such cells has not been described.

"Putrescine" is a non-protein coding amino acid, a polyamine, involved in the urea cycle. Putrescine (also known as 1,4-Diaminobutane, having a chemical formula of $C_4H_{12}N_2$) is produced by the decarboxylation of ornithine and serves as a precursor to gamma-aminobutyrate (γ-aminobutyrate).

As used herein "peptide", "polypeptide" and "protein" are used interchangeably throughout and refer to a molecule comprising two or more amino acid residues joined to each other by a peptide bond. Peptides, polypeptides and proteins may also include modifications such as glycosylation, lipid attachment, sulfation, gamma-carboxylation of glutamic acid residues, alkylation, hydroxylation and ADP-ribosylation. Peptides, polypeptides, and proteins can be of scientific or commercial interest, including protein-based drugs (biotherapeutics). Peptides, polypeptides, and proteins include, among other things, antibodies and chimeric or fusion proteins. Peptides, polypeptides, and proteins can be produced by recombinant animal cell lines such as mammalian cell lines using cell culture methods.

The term "polynucleotide sequence" or "peptide sequence", as used herein refers to nucleic acid polymers encoding proteins of interest, such as chimeric proteins (like trap molecules), antibodies or antibody portions (e.g., VH, VL, CDR3) that are produced as a biopharmaceutical drug substance. The polynucleotide sequence may be manufactured by genetic engineering techniques (e.g., a sequence encoding a chimeric protein, or a codon-optimized sequence, an intron-less sequence) and introduced into a cell, where it may reside as an episome or be integrated into the genome of the cell. The polynucleotide sequence may be a naturally occurring sequence that is introduced into an ectopic site within the host cell genome. The peptide sequence may be heterologous, such as a naturally occurring sequence from another organism, a recombinant sequence, a genetically modified sequence, or inter alia a sequence expressed under the control of a different-than-wild type promoter, for example a nucleotide sequence encoding a human ortholog, whereby the host (production) cell is a CHO cell.

The phrase "antigen-binding protein" includes a protein that has at least one CDR and is capable of selectively recognizing an antigen, i.e., is capable of binding an antigen with a KD that is at least in the micromolar range. Therapeutic antigen-binding proteins (e.g., therapeutic antibodies) frequently require a KD that is in the nanomolar or the picomolar range. Typically, an antigen-binding protein includes two or more CDRs, e.g., 2, 3, 4, 5, or 6 CDRs. Examples of antigen binding proteins include antibodies, antigen-binding fragments of antibodies such as polypeptides containing the variable regions of heavy chains and light chains of an antibody (e.g., Fab fragment, F(ab')2 fragment), and proteins containing the variable regions of heavy chains and light chains of an antibody and containing additional amino acids from the constant regions of heavy and/or light chains (such as one or more constant domains, i.e., one or more of CL, CHI, hinge, CH2, and CH3 domains).

"Antibody" refers to an immunoglobulin molecule consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains three domains, CH1, CH2 and CH3. Each light chain has a light chain variable region (VL) and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from the amino-terminus to the carboxy-terminus in the following order: FR1, CDR1, FR2, CDR2, FR3, CDR3, and FR4. The term "antibody" includes both glycosylated and non-glycosylated immunoglobulins of any isotype or subclass. The term "antibody" includes antibody molecules prepared, expressed, created or isolated by recombinant means, such as antibodies isolated from a host cell transfected with a nucleotide sequence in order to express the antibody. The term "antibody" also includes a bispecific antibody, which includes a heterotetrameric immunoglobulin that can bind to more than one epitope. Bispecific antibodies are generally described in U.S. Patent Application Publication No. 2010/0331527, which is incorporated by reference herein.

The term "antigen-binding portion" of an antibody (or antibody fragment) or a protein of interest refers to one or more fragments of an antibody or a protein of interest that retain the ability to specifically bind to an antigen. Non-limiting examples of protein binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., Nature (1989) 241:544-546), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody". See, e.g., Holliger et al., PNAS USA (1993) 90:6444-6448; Poljak et al., Structure (1994) 2:1121-1123.

Still further, an antibody or antigen-binding portion thereof may be part of a larger immunoadhesion molecule, formed by covalent or noncovalent association of the antibody or antibody portion with one or more other proteins or peptides. Non-limiting examples of such immunoadhesion molecules include use of the streptavidin core region to make a tetrameric scFv molecule (Kipriyanov et al., Human Antibodies and Hybridomas (1995) 6:93-101) and use of a cysteine residue, a marker peptide and a C-terminal polyhistidine tag to make bivalent and biotinylated scFv molecules (Kipriyanov et al. Mol. Immunol. (1994) 31:1047-1058). Antibody portions, such as Fab and F(ab')2 fragments, can be prepared from whole antibodies using conventional techniques, such as via papain or pepsin digestion of whole antibodies. Moreover, antibodies, antibody portions and immunoadhesion molecules can be obtained using standard recombinant DNA techniques commonly known in the art (see Sambrook et al., 1989).

The term "human antibody" is intended to include antibodies having variable and constant regions derived from human germline immunoglobulin sequences. Human antibodies of the present disclosure may include amino acid residues not encoded by human germline immunoglobulin sequences (e.g., mutations introduced by random or site-specific mutagenesis in vitro or by somatic mutation in vivo), for example in the CDRs and in particular CDR3. The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see, e.g., Taylor et al. Nucl. Acids Res. (1992) 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis), and thus the amino acid sequences of the VH and VL regions of the recombinant antibodies are sequences that, while derived from and related to human germline VH and VL sequences, may not naturally exist within the human antibody germline repertoire in vivo.

"Fc fusion proteins" comprise part or all of two or more proteins, one of which is an Fc portion of an immunoglobulin molecule, which are not otherwise found together in nature. Preparation of fusion proteins comprising certain heterologous polypeptides fused to various portions of antibody-derived polypeptides (including the Fc domain) has been described, e.g., by Ashkenazi et al., PNAS USA (1991) 88:10535; Byrn et al., Nature (1990) 344:677; and Hollenbaugh et al., Current Protocols in Immunology (1992) Suppl. 4, pp. 10.19.1-10.19.11. "Receptor Fc fusion proteins" comprise one or more extracellular domain(s) of a receptor coupled to an Fc moiety, which in some embodiments comprises a hinge region followed by a CH2 and CH3 domain of an immunoglobulin. In some embodiments, the Fc-fusion protein contains two or more distinct receptor chains that bind to a one or more ligand(s).

In certain embodiments, an "Fc-fusion protein" is a "trap" molecule, which is a decoy receptor molecule that includes two distinct receptor components that mimic the binding domains of a corresponding endogenous receptor and the Fc portion of an antibody. Non-limiting examples of trap molecules include an IL-1 trap (e.g., rilonacept, which contains the IL-IRAcP ligand binding region fused to the IL-1R1 extracellular region which in turn is fused to the Fc of hlgG1) (e.g., SEQ ID NO: 1) (see U.S. Pat. No. 6,927,004), or a VEGF trap (e.g., aflibercept, which contains the Ig domain 2 of the VEGF receptor Flt1 fused to the Ig domain 3 of the VEGF receptor Flk1 which in turn is fused to Fc of hlgG1. See, e.g., U.S. Pat. Nos. 7,087,411, 7,279,159; see also U.S. Pat. No. 5,610,279 for etanercept (TNF trap).

"Glycosylation" includes the formation of glycoproteins where oligosaccharides are attached either to the side chain of an asparagine (Asn) residue (i.e., N-linked), or a serine (Ser) or threonine (Thr) residue (i.e., O-linked) of a protein. “Glycoproteins” include any protein that contains an O-linked glycan or an N-linked glycan. Glycans can be homo- or heteropolymers of monosaccharide residues, which can be linear or branched. N-linked glycosylation is known to initiate primarily in the endoplasmic reticulum, whereas O-linked glycosylation is shown to initiate in either the ER or Golgi apparatus. The term “N-glycan” is used interchangeably with “N-linked oligosaccharide.” The term “O-glycan” is used interchangeably with “O-linked oligosaccharide.”

An “N-glycan protein” includes proteins that contain or can accept N-linked oligosaccharides. N-glycans can be composed of N-acetyl galactosamine (GalNAc), mannose (Man), fucose (Fuc), galactose (Gal), neuraminic acid (NANA), and other monosaccharides, however N-glycans usually have a common core pentasaccharide structure including: three mannose and two N-acetylglucosamine (GlcNAc) sugars. Proteins with the consecutive amino acid sequence, Asn-X-Ser or Asn-X-Thr, where X is any amino acid except proline, can provide an attachment site for N-glycans.

N-glycans include those N-linked oligosaccharides listed in Table 1. The shorthand designations of the listed oligosaccharides are used herein as simplified names to describe the oligosaccharide. Thus for example, an A1 N-glycan contains an arginine linked to a oligosaccharide consisting of (SA) (Gal)2(GlcNAc)2(Man)3(GlcNAc) 3.

TABLE 1

N-Linked Oligosaccharides

| Name of Molecule* | Shorthand Designation | Expected Mass (g/mol) | Graphic Depiction** |
|---|---|---|---|
| (SA)(Gal)2(GlcNAc)2(Man)3(GlcNAc)3 | A1 | 2051.7 | 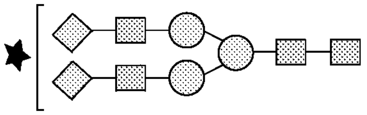 |
| (SA)(Gal)2(GlcNAc)2(Man)3(GlcNAc)3(Fuc) | A1F | 2197.7 | 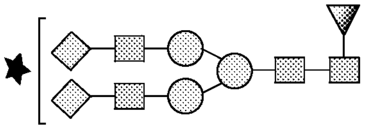 |
| (SA)2(Gal)2(GlcNAc)2(Man)3(GlcNAc)3 | A2 | 2343.2 | 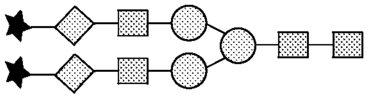 |
| (SA)2(Gal)2(GlcNAc)2(Man)3(GlcNAc)3(Fuc) | A2F | 2488.8 | 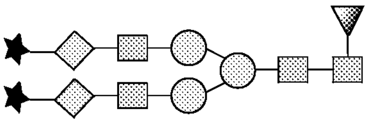 |
| (Man)5(GlcNAc)2 | Man5 | 1354.4 | 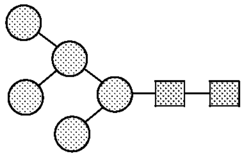 |
| (Gal)2(GlcNAc)2(Man)3(GlcNAc)3 | NA2 | 1760.6 | 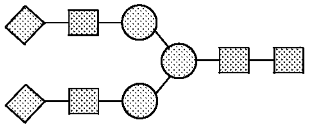 |
| (Gal)2(GlcNAc)2(Man)3(GlcNAc)3(Fuc) | NA2F | 1906.6 | 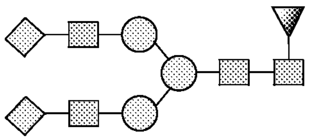 |
| (Gal)(GlcNAc)2(Man)3(GlcNAc)3 | NA2G1 | 1598.5 | 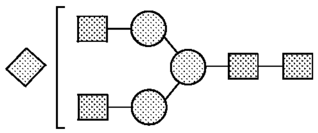 |

TABLE 1-continued

| N-Linked Oligosaccharides | | | |
|---|---|---|---|
| Name of Molecule* | Shorthand Designation | Expected Mass (g/mol) | Graphic Depiction** |
| (Gal)(GlcNAc)2(Man)3(GlcNAc)3(Fuc) | NA2G1F | 1744.1 | 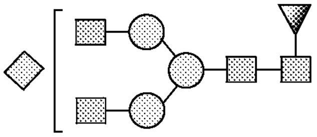 |
| (GlcNAc)2(Man)3(GlcNAc)2 | NGA2 | 1436.5 | 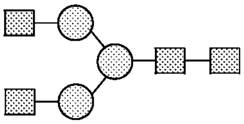 |
| (GlcNAc)2(Man)3(GlcNAc)2(Fuc) | NGA2F | 1582.5 | 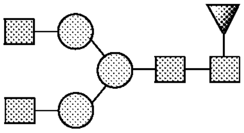 |

*Abbreviations for monosaccharides are sialic acid (SA), galactose (Gal), mannose (Man), GlcNAc (N-acetylglucosamine), and fucose (Fuc).

**Glycan key: triangle = fucose; square = N-acetyl glucosamine; circle = mannose; star = sialic acid.

Screening

"Hydrolysates" are complex materials derived from the hydrolysis of plant material, animal material, whey, yeast, and the like. The term "hydrolysate" is used interchangeably with "protein hydrolysate". "Plant hydrolysates" (plant protein hydrolysates) are hydrolysed plant material such as rice flour, wheat flour, corn flour, soy flour, and the like. Protein hydrolysates can be manufactured by three general methods: acid hydrolysis, alkaline hydrolysis, and enzymatic hydrolysis. For biological applications, including biotherapeutic manufacturing, protein hydrolysates are mostly made by enzymatic hydrolysis. For example, a soy hydrolysate made by pepsin digestion may be called "soy peptone", or a yeast hydrolysate made by trpsin digestion may be called "yeast tryptone." Franek et al., Biotechnol. Prog. 16 (5): 688-92 (2000) is incorporated herein for plant protein hydrolysates and methods of manufacturing them.

In some embodiments, the subject hydrolysate is a plant hydrolysate. In a specific embodiment, the subject protein hydrolysate is a soy hydrolysate. "Soy hydrolysate" is an enzymatically digested soy product derived from soybean grit, that is largely, chemically undefined. Generally, soy hydrolysate is composed of a conglomerate of amino acids, proteins, carbohydrates, minerals and vitamins. Soy hydrolysate is a plant-derived protein hydrolysate that is commercially available, for example, in high concentration solution (e.g., HyClone™ HyQ Soy Hydrolysate solution) or powder (e.g., Sigma Aldrich® S1674 (Amisoy™), soy protein hydrolysate) form. A "batch" or "lot" of soy hydrolysate, as used herein refers to a manufactured amount of soy hydrolysate resulting from hydrolysis of soybean grit. For example, each hydrolysis process can result in a unique "batch" or "lot" of soy hydrolysate with varying concentrations of components, such as vitamins, amino acids, peptides and sugars. Soy hydrolysate is commonly used with animal protein-free cell culture medium for the growth of mammalian cell lines during the production of commercial biotherapeutics, such as antibodies. More specifically, soy hydrolysate is added to a cell culture media prior to or during inoculation with cells. The cells are then cultured in the hydrolysate-containing medium, until they are harvested. Due to the undefined nature of soy hydrolysate, batches of soy hydrolysate will vary from batch-to-batch (or lot-to-lot), which can lead to inconsistencies in commercial manufacturing of biotherapeutics.

The present disclosure has identified that concentrations of certain components in a batch of soy hydrolysate affect the quality and composition of proteins produced in cell culture using soy hydrolysate. The present disclosure provides methods for screening batches of soy hydrolysate in order to select certain batches of soy hydrolysate that contain a desirable amount of a component such as, for example, ornithine, putrescine, citrulline, arginine or a combination thereof.

In certain embodiments, the screening method includes measuring the amount of ornithine or putrescine in at least a portion (i.e., a sample) of a batch of soy hydrolysate. In a specific embodiment, a soy hydrolysate sample is weighed and a portion thereof is dissolved to a desired concentration. In some embodiments, the soy hydrolysate solution is then diluted in a solvent to a second desired concentration (e.g., 1 g/L to 25 g/L) and the composition of the resulting soy hydrolysate solutions can then be determined.

In some embodiments, the measuring step employs a suitable method for determining the molecular composition of a soy hydrolysate sample including, for example, colorimetric detection performed following post-column ninhydrin reaction, or chromatography f eluted ninhydrin-positive compounds, such as HPLC or UPLC, and the units used to express the measured amount of each component (e.g., ornithine or putrescine) can be any suitable units (e.g., micromoles/L, mg/L or g/L). In some embodiments, measuring the amount of ornithine or putrescine includes measuring the concentration of ornithine in a sample or measuring the total amount of ornithine in a soy hydrolysate sample. However, an amount of ornithine or putrescine is measured and whatever units are used to express the measured amount, the concentration of ornithine or putrescine in the selected batch of soy hydrolysate is less than or equal to 0.67 mg ornithine or putrescine per g soy.

In one embodiment, a sample of a batch of soy hydrolysate is obtained and the ornithine or putrescine contents of the sample are measured by chromatography of the amino acids on an ion exchange column with post column ninhydrin detection. More specifically, in a specific embodiment screening methods include acid hydrolysis of a soy hydrolysate sample and reconstitution in a sample buffer. The hydrolyzed sample is then subject to high performance cation exchange separation on, for example, a column of a sulphonated polystyrene resin (Dowex 50) followed by a post-column derivatization that allows sensitive detection of individual amino acids within a sample. See, e.g., Moore and Stein. J. Biol. Chem. (1954) Vol. 211 pp. 907-913; Nemkov, et al., Amino Acids 2015 November; 47 (11): 2345-2357; Wahl and Holzgrabe, "Amino acid analysis for pharmacopeial purposes," Talanta 154:150-163, 1 Jul. 2016. Following post-column color development by Ninhydrin reagent, absorbance is measured in the ninhydrin purple range, e.g., 570 nm. Data acquisition is accomplished using chromatography software (e.g., EZChrom Elite for Hitachi version 3.1.5b chromatography software) to provide a quantitative chromatogram showing micromoles/L per amino acid, mg/L per amino acid, or g/L per amino acid.

One of ordinary skill in the art will appreciate that other methods for the identification and measurement of amino acids in a sample composition can be used in accordance with the methods of the presence disclosure, such as pre-column derivatization chromatography or reverse phase liquid chromatography methods using liquid chromatography and mass spectroscopy.

In certain embodiments, liquid chromatography-mass spectrometry is used to screen a soy hydrolysate sample. For example, a sample of a batch of soy hydrolysate may be obtained as set forth herein and subjected to a chromatography run, or series of chromatography runs on a high-performance liquid chromatography (HPLC) system, such as Agilent 1100 or Agilent 1200SL. Mass spectrometry analysis can be carried out to provide high-resolution quantitative data describing the composition of the soy hydrolysate sample being measured.

In some embodiments, the present disclosure provides a method that includes screening batches of soy hydrolysate for a desired amount of a component, such as ornithine, putrescine and/or citrulline, and selecting those batches of soy hydrolysate that have a desired amount of such component. For example, a sample including a portion of a batch of soy hydrolysate powder can be screened as described above, and compared to an amino acid standard profile generated under the same conditions as the sample run. As shown in FIGS. 1A-1B, the resulting chromatogram(s) will provide the concentration of each amino acid component present in the soy hydrolysate sample (e.g., micromoles/L per amino acid, mg/L per amino acid, or g/L per amino acid). Analyzing the chromatogram, facilitates identification of batches of soy hydrolysate (i.e., samples) that contain a desired concentration of a component, such as ornithine, putrescine and/or citrulline. Each batch of soy hydrolysate that includes a desired amount of a specific component or components is then selected for further use, e.g., in cell culture, as describe herein. FIG. 1, panel A depicts a rejected batch following amino acid identification. FIG. 1, panel B depicts an example of an acceptable soy hydrolysate batch run under identical conditions. The amino acid peak corresponding to ornithine is circled in both figures. The concentration of ornithine or putrescine can be determined generating a standard curve and interpolating the sample ornithine or putrescine concentration. Alternatively, the relative amount of ornithine or putrescine can be determined by determining the area under the curve for the ornithine or putrescine peak and dividing it by the total of the areas under the peak for all amino acids, or comparing the peak area to a standard.

In certain embodiments, the desired concentration of the component of soy hydrolysate (e.g., ornithine or putrescine) to be selected is 5 mg/L or less. In one embodiment, the desired concentration of ornithine or putrescine in a batch of soy hydrolysate to be selected ranges from 0.5 mg/L to 5.0 mg/L or from 0.5 mg/L to 2.0 mg/L. In other embodiments, the concentration of ornithine or putrescine in a selected batch of soy hydrolysate ranges from 0.5 mg/L to 4.5 mg/L, 0.5 mg/L to 4.0 mg/L, 0.5 mg/L to 3.5 mg/L, 0.5 mg/L to 3.0 mg/L, 0.5 mg/L to 2.5 mg/L, 0.5 mg/L to 2.0 mg/L, 0.5 mg/L to 1.5 mg/L or 0.5 mg/L to 1.0 mg/L. In some embodiments, the concentration of ornithine or putrescine in a selected batch of soy hydrolysate ranges from 1.0 mg/L to 5.0 mg/L, 1.5 mg/L to 5.0 mg/L, 2.0 mg/L to 5.0 mg/L, 2.5 mg/L to 5.0 mg/L, 3.0 mg/L to 5.0 mg/L, 3.5 mg/L to 5.0 mg/L, 4.0 mg/L to 5.0 mg/L or 4.5 mg/L to 5.0 mg/L.

In specific embodiments, the desired concentration of ornithine or putrescine in a batch of soy hydrolysate is at least 0.5 mg/L, 0.6 mg/L, 0.7 mg/L, 0.8 mg/L, 0.9 mg/L, 1.1 mg/L, 1.2 mg/L, 1.3 mg/L, 1.4 mg/L, 1.5 mg/L, 1.6 mg/L, 1.7 mg/L, 1.8 mg/L, 1.9 mg/L, 2.0 mg/L, 2.1 mg/L, 2.2 mg/L, 2.3 mg/L, 2.4 mg/L, 2.5 mg/L, 2.6 mg/L, 2.7 mg/L, 2.8 mg/L, 2.9 mg/L, 3.0 mg/L, 3.1 mg/L, 3.2 mg/L, 3.3 mg/L, 3.4 mg/L, 3.5 mg/L, 3.6 mg/L, 3.7 mg/L, 3.8 mg/L, 3.9 mg/L, 4.0 mg/L, 4.1 mg/L, 4.2 mg/L, 4.3 mg/L, 4.4 mg/L, 4.5 mg/L, 4.6 mg/L, 4.7 mg/L, 4.8 mg/L, 4.9 mg/L, or is 5.0 mg/L ornithine or putrescine.

In other embodiments, the desired concentration of ornithine or putrescine in a batch of soy hydrolysate is not more than 0.67 mg ornithine per g soy. In still other embodiments, the desired concentration of ornithine or putrescine in a batch of soy hydrolysate is not more than 0.27 mg ornithine per g soy. In another embodiment, the desired concentration of ornithine or putrescine in a batch of soy hydrolysate is not more than 0.24 mg ornithine or putrescine per g soy. In some embodiments, the desired concentration of ornithine or putrescine in a batch of soy is from 0.067 mg to 0.67 mg ornithine or putrescine per g soy. In still other embodiments, the desired concentration of ornithine or putrescine in a batch of soy hydrolysate falls with the range of 0.067 mg to 0.27 mg ornithine per g soy. In yet another embodiment, the desired concentration of ornithine or putrescine in a batch of soy hydrolysate falls with the range of 0.067 mg to 0.24 mg ornithine or putrescine per g soy.

In one embodiment, the relative amount by mass of ornithine or putrescine (% w/w) in the selected soy hydrolysate (w/w=mass of ornithine or putrescine/total mass of hydrolysate) is ≤0.067%, such as 0.0001%, 0.0002%, 0.0003%, 0.0004%, 0.0005%, 0.0006%, 0.0007%, 0.0008%, 0.0009%, 0.001%, 0.0015%, 0.002%, 0.0025%, 0.003%, 0.0035%, 0.004%, 0.0045%, 0.005%, 0.0055%, 0.006%, 0.0061%, 0.0062%, 0.0063%, 0.0064%, 0.0065%, 0.0066%, all by w/w.

In one embodiment, the plant protein hydrolysate is selected on the basis of producing a glycoprotein with a specific quality attribute. The quality of glycoprotein may be determined by assessing the level of one or more specific N-glycans on the glycoprotein, or by assessing the level of one or more specific sugars on the glycoprotein, or a combination of multiple attributes. For example, a glycoprotein having a specific fucose level, e.g., 5-10 moles of fucose per mole of glycoprotein, can be a quality attribute criterion; or a specific sialic acid level, e.g., 5-15 moles of sialic acid per mole of glycoprotein; or a specific ratio of A1 N-glycan per total of all N-glycans, e.g., 10-17% (w/w) can be considered to have the requisite quality attribute. A plant protein hydrolysate enabling the production of said glycoprotein would be considered selectable.

In one embodiment, the plant protein hydrolysate is selected by producing a glycoprotein in a cell cultured in a medium containing the potential selected (potentially selectable) plant protein hydrolysate (e.g., soy hydrolysate), purifying the glycoprotein, subjecting the glycoprotein to oligosaccharide fingerprinting, and determining the relative amount of A1 N-glycan by calculating the area under the peak associated with the A1 N-glycan and dividing that value by the total area under the peaks of all N-glycans, and selecting a plant protein hydrolysate that enabled the production of a glycoprotein with a relative amount of A1 N-glycan of ≥10%, ≥10.5%, 10-17%, 10%, 10.5%, 11%, 11.5%, 12%, 12.5%, 13%, 13.5%, 14%, 14.5%, 15%, 15.5%, 16%, 16.5%, 17%, 17.5%, or 18%.

Cell Culture

The present disclosure provides a method for culturing cells expressing a protein of interest in a cell culture medium using a selected batch of soy hydrolysate as described above. The instant disclosure has found, for the first time, that the use of selected batches of soy hydrolysate comprising 5.0 mg/L ornithine or less in cell culture media reduces lot-to-lot variability and improves protein product quality. The instant disclosure has found, for the first time, that the use of selected batches of soy hydrolysate comprising 5.0 mg/L putrescine or less in cell culture media reduces lot-to-lot variability and improves protein product quality.

"Cell culture" or "culture" means the growth and propagation of cells outside of a multicellular organism or tissue. Suitable culture conditions for mammalian cells are known in the art. See, e.g., Animal cell culture: A Practical Approach, D. Rickwood, ed., Oxford University Press, New York (1992). Mammalian cells may be cultured in suspension or while attached to a solid substrate. Fluidized bed bioreactors, hollow fiber bioreactors, roller bottles, shake flasks, or stirred tank bioreactors, with or without microcarriers, and operated in a batch, fed batch, continuous, semi-continuous, or perfusion mode are available for mammalian cell culture. Cell culture media or concentrated feed media may be added to the culture continuously or at intervals during the culture. For example, a culture may be fed once per day, every other day, every three days, or may be fed when the concentration of a specific medium component, which is being monitored, falls outside a desired range.

As used herein, the terms "cell culture media", "media", "cell media", "cell culture medium" or "culture medium" refers to any nutrient solution used for growing cells, e.g., animal or mammalian cells, and which generally provides at least one or more components from the following: an energy source (usually in the form of a carbohydrate such as glucose); one or more of all essential amino acids, and generally the twenty basic amino acids, plus cysteine; vitamins and/or other organic compounds typically required at low concentrations; lipids or free fatty acids; and trace elements, e.g., inorganic compounds or naturally occurring elements that are typically required at very low concentrations, usually in the micromolar range. In some embodiments, a cell culture media is formed by combining a soy or other plant protein hydrolysate with an additional ingredient.

As used herein, "additional ingredient" includes any one or more of cell culture media components including but not limited to water, an energy source, one or more of all essential amino acids, and generally the twenty basic amino acids, plus cysteine; vitamins and/or other organic compounds typically required at low concentrations, lipids or free fatty acids, and trace elements.

In specific embodiments, the cell culture media is supplemented with an amount of a selected batch of soy hydrolysate. In certain embodiments, the cell culture medium is supplemented with about 0.5 g/L to about 25 g/L of a selected soy hydrolysate. In some embodiments, the cell culture medium is supplemented with about 0.5 g/L, 1 g/L, 1.5 g/L, 2 g/L, 2.5 g/L, 2 g/L, 2.5 g/L, 3 g/L, 3.5 g/L, 4 g/L, 4.5 g/L, 5 g/L, 5.5 g/L, 6 g/L, 6.5 g/L, 7 g/L, 7.5 g/L, 8 g/L, 8.5 g/L, 9 g/L, 9.5 g/L, 10 g/L, 10.5 g/L, 11 g/L, 11.5 g/L, 12 g/L, 12.5 g/L, 13 g/L, 13.5 g/L, 14 g/L, 14.5 g/L, 15 g/L, 15.5 g/L, 16 g/L, 16.5 g/L, 17 g/L, 17.5 g/L, 18 g/L, 18.5 g/L, 19 g/L, 19.5 g/L, 20 g/L, 20.5 g/L, 21 g/L, 21.5 g/L, 22 g/L, 22.5 g/L, 23 g/L, 23.5 g/L, 24 g/L, 24.5 g/L, or about 25 g/L of a selected batch of soy hydrolysate.

In one embodiment, the concentration of ornithine or putrescine in the cell culture media after addition of the plant protein hydrolysate is ≤5 mg/L, 0.6-3 mg/L, 0.01 mg/L, 0.02 mg/L, 0.03 mg/L, 0.04 mg/L, 0.05 mg/L, 0.06 mg/L, 0.07 mg/L, 0.08 mg/L, 0.09 mg/L, 0.010 mg/L, 0.015 mg/L, 0.02 mg/L, 0.025 mg/L, 0.03 mg/L, 0.035 mg/L, 0.04 mg/L, 0.045 mg/L, 0.05 mg/L, 0.055 mg/L, 0.06 mg/L, 0.065 mg/L, 0.07 mg/L, 0.075 mg/L, 0.08 mg/L, 0.085 mg/L, 0.09 mg/L, 0.095 mg/L, 0.1 mg/L, 0.15 mg/L, 0.2 mg/L, 0.25 mg/L, 0.3 mg/L, 0.35 mg/L, 0.4 mg/L, 0.45 mg/L, 0.5 mg/L, 0.55 mg/L, 0.6 mg/L, 0.65 mg/L, 0.7 mg/L, 0.75 mg/L, 0.8 mg/L, 0.85 mg/L, 0.9 mg/L, 0.95 mg/L, 1 mg/L, 1.5 mg/L, 2 mg/L, 2.5 mg/L, 3 mg/L, 3.5 mg/L, 4 mg/L, 4.5 mg/L, or 5 mg/L.

In one embodiment, the cells being cultured are cells of a cell line capable of producing a biotherapeutic protein. Non-limiting examples of cell lines that are used to produce protein biotherapeutics include inter alia primary cells, BSC cells, HeLa cells, HepG2 cells, LLC-MK cells, CV-1 cells, COS cells, VERO cells, MDBK cells, MDCK cells, CRFK cells, RAF cells, RK cells, TCMK-1 cells, LLCPK cells, PK15 cells, LLC-RK cells, MDOK cells, BHK cells, BHK-21 cells, CHO cells, CHO-K1 cells, NS-1 cells, MRC-5 cells, WI-38 cells, BHK cells, 3T3 cells, 293 cells, RK cells, Per.C6 cells and chicken embryo cells. In one embodiment, the cell line is a CHO cell line or one or more of several specific CHO cell variants optimized for large-scale protein production, e.g., CHO-K1, or the CHO-K1-derived EESYR® (enhanced expression and stability regions) cells (U.S. Pat. No. 7,771,997).

In one embodiment, the cells that are cultured and express the heterologous glycoprotein are a population of cells obtained by clonal expansion of a cell (i.e., the progenitor cell) that harbors and expresses a polynucleotide encoding the glycoprotein or a subunit of the glycoprotein, where the glycoprotein is a complex multi-subunit protein like an antibody. In some embodiments at least 50%, at least 60%, at least 70%, at least 80%, at least 90%, at least 95%, at least 98%, at least 99%, or about 100% of the constituent cells of the population of cells obtained or descended by clonal expansion from the progenitor cell contain the glycoprotein-encoding polynucleotide and express the glycoprotein.

Mammalian cells, such as CHO cells, may be cultured in small scale cell culture containers, such as in 125 ml containers having about 25 ml of media, 250 ml containers having about 50 to 100 ml of media, 500 ml containers having about 100 to 200 ml of media. Alternatively, the cultures can be large scale such as for example 1000 ml containers having about 300 to 1000 ml of media, 3000 ml containers having about 500 ml to 3000 ml of media, 8000 ml containers having about 2000 ml to 8000 ml of media, and 15000 ml containers having about 4000 ml to 15000 ml of media. Cultures for manufacturing (i.e., production cell cultures) can contain 10,000 L of media or more. Large scale cell cultures or "production cell cultures", such as for clinical manufacturing of protein therapeutics, are typically maintained for days, or even weeks, while the cells produce the desired protein(s). During this time the culture can be supplemented with a concentrated feed medium containing components, such as nutrients and amino acids, which are consumed during the course of the culture.

In certain embodiments, a concentrated feed medium is used. Concentrated feed medium may be based on any cell culture media formulation. Such a concentrated feed medium can contain most of the components of a cell culture medium described herein at, for example, about 5×, 6×, 7×, 8×, 9×, 10×, 12×, 14×, 16×, 20×, 30×, 50×, 100×, 200×, 400×, 600×, 800×, or even about 1000× of their normal useful amount. Concentrated feed media are often used in fed batch culture processes.

In some embodiments, the cell culture media is supplemented with "point-of-use additions", also known as additions, point-of-use ingredients, or point-of-use chemicals, during the course of cell growth or protein production. Point-of-use additions include any one or more of a growth factor or other proteins, a buffer, an energy source, a salt, an amino acid, a metal, and a chelator. Other proteins include transferrin and albumin. Growth factors, which include cytokines and chemokines, are generally known in the art and are known to stimulate cell growth, or in some cases, cellular differentiation. A growth factor is usually a protein (e.g., insulin), a small peptide, or a steroid hormone, such as estrogen, DHEA, testosterone, and the like. In some cases, a growth factor may be a non-natural chemical that promotes cell proliferation or protein production, such as e.g., tetrahydrofolate (THF), methotrexate, and the like. Non-limiting examples of protein and peptide growth factors include angiopoietins, bone morphogenetic proteins (BMPs), brain-derived neurotrophic factor (BDNF), epidermal growth factor (EGF), erythropoietin (EPO), fibroblast growth factor (FGF), glial cell line-derived neurotrophic factor (GDNF), granulocyte colony-stimulating factor (G-CSF), granulocyte macrophage colony-stimulating factor (GM-CSF), growth differentiation factor-9 (GDF9), hepatocyte growth factor (HGF), hepatoma-derived growth factor (HDGF), insulin, insulin-like growth factor (IGF), migration-stimulating factor, myostatin (GDF-8), nerve growth factor (NGF) and other neurotrophins, platelet-derived growth factor (PDGF), thrombopoietin (TPO), transforming growth factor alpha (TGF-α), transforming growth factor beta (TGF-β), tumor necrosis factor-alpha (TNF-α), vascular endothelial growth factor (VEGF), wnt signaling pathway agonists, placental growth factor (PIGF), fetal Bovine somatotrophin (FBS), interleukin-1 (IL-1), IL-2, IL-3, IL-4, IL-5, IL-6, IL-7, and the like. In one embodiment, the cell culture media is supplemented with the point-of-use addition growth factor insulin. In one embodiment, the concentration of insulin in the media, i.e., the amount of insulin in the cell culture media after addition is from about 0.1 μM to 10 μM. One or more the point-of-use additions can also be included in the media formulation of some embodiments.

Buffers are generally known in the art. The invention is not restricted to any particular buffer or buffers, and any one of ordinary skill in the art can select an appropriate buffer or buffer system for use with a particular cell line producing a particular protein. In one embodiment, a point-of-use addition buffer is NaHCO3/CO2 system. In one embodiment, the point-of-use addition buffer comprises NaHCO3. In another embodiment, the buffer is HEPES.

Energy sources for use as a point-of-use addition in cell culture are also well known in the art. Without limitation, in one embodiment, the point-of-use addition energy source is glucose. Given the particular and specific requirements of a particular cell line and the protein to be produced, in one embodiment the glucose can be added to a concentration of about 1 to 20 mM in the media.

Chelators are likewise well known in the art of cell culture and protein production. Tetrasodium EDTA dehydrate and citrate are two common chelators used in the art, although other chelators may be employed in the practice of this invention. In one embodiment, a point-of-use addition chelator is tetrasodium EDTA dihydrate. In one embodiment, a point-of-use addition chelator is citrate, such as Na3C6H5O7.

In one embodiment, the cell culture may be supplemented with one or more point-of-use addition amino acids such as, glutamine. Other point-of-use additions include one or more of various metal salts, such as salts of iron, nickel, zinc and copper. In one embodiment, the cell culture media is supplemented with any one or more of copper sulfate, zinc sulfate, ferric chloride; and nickel sulfate.

In one embodiment, the media is supplemented at intervals during cell culture according to a fed-batch process. Fed-batch culturing is generally known in the art and employed to optimized protein production. See, e.g., Y. M. Huang et al., Biotechnol Prog. (2010) 26 (5) pp. 1400-1410.

In another aspect of the present disclosure, cells cultured in medium comprising soy hydrolysate containing ornithine or putrescine at a desired concentration (i.e., less than or equal to 5.0 mg/L, e.g., from 0.5 mg/L to 5.0 mg/L or from 0.5 mg/L to 2.0 mg/L) produce a protein of interest with improved quality, as compared to cells cultured in medium comprising soy hydrolysate containing ornithine or putrescine at a concentration of greater than 5 mg/L. In certain embodiments, improved protein quality is measured by: the presence or absence of glycosylation at one or more amino acids on the protein of interest, the amount of glycan on the protein of interest, the presence of sialic acid at one or more glycosylation sites on the protein of interest, or a combination thereof. As used herein "enhanced quality", "improved quality" or "high quality" protein product can also refer to the more consistent quality, for example, post-translational modifications observed in a biotherapeutic protein production lot. Consistent quality includes having, for example, a repeatable desired glycosylation profile after replicate production lines. Consistency, with respect to quality, refers to a degree of uniformity and standardization, whereas replicate production batches are essentially free from variation.

In certain embodiments, the protein product (protein of interest) is an antibody, a human antibody, a humanized antibody, a chimeric antibody, a monoclonal antibody, a multispecific antibody, a bispecific antibody, an antigen binding antibody fragment, a single chain antibody, a diabody, triabody or tetrabody, a Fab fragment or a F(ab')2 fragment, an IgD antibody, an IgE antibody, an IgM antibody, an IgG antibody, an IgG1 antibody, an IgG2 antibody, an IgG3 antibody, or an IgG4 antibody. In one embodiment, the antibody is an IgG1 antibody. In one embodiment, the antibody is an IgG2 antibody. In one embodiment, the antibody is an IgG4 antibody. In one embodiment, the antibody is a chimeric IgG2/IgG4 antibody. In one embodiment, the antibody is a chimeric IgG2/IgG1 antibody. In one embodiment, the antibody is a chimeric IgG2/IgG1/IgG4 antibody.

In some embodiments, the antibody is selected from the group consisting of an anti-Programmed Cell Death 1 antibody (e.g., an anti-PD1 antibody as described in U.S. Pat. Appln. Pub. No. US2015/0203579A1), an anti-Programmed Cell Death Ligand-1 (e.g., an anti-PD-L1 antibody as described in U.S. Pat. Appln. Pub. No. US2015/0203580A1), an anti-Dl14 antibody, an anti-Angiopoetin-2 antibody (e.g., an anti-ANG2 antibody as described in U.S. Pat. No. 9,402,898), an anti-Angiopoetin-Like 3 antibody (e.g., an anti-AngPt13 antibody as described in U.S. Pat. No. 9,018,356), an anti-platelet derived growth factor receptor antibody (e.g., an anti-PDGFR antibody as described in U.S. Pat. No. 9,265,827), an anti-Erb3 antibody, an anti-Prolactin Receptor antibody (e.g., anti-PRLR antibody as described in U.S. Pat. No. 9,302,015), an anti-Complement 5 antibody (e.g., an anti-$C_5$ antibody as described in U.S. Pat. Appln. Pub. No US2015/0313194A1), an anti-TNF antibody, an anti-epidermal growth factor receptor antibody (e.g., an anti-EGFR antibody as described in U.S. Pat. No. 9,132,192 or an anti-EGFRvIII antibody as described in U.S. Pat. Appln. Pub. No. US2015/0259423A1), an anti-Proprotein Convertase Subtilisin Kexin-9 antibody (e.g. an anti-PCSK9 antibody as described in U.S. Pat. No. 8,062,640 or U.S. Pat. Appln. Pub. No. US2014/0044730A1), an anti-Growth And Differentiation Factor-8 antibody (e.g., an anti-GDF8 antibody, also known as anti-myostatin antibody, as described in U.S. Pat. No. 8,871,209 or 9,260,515), an anti-Glucagon Receptor (e.g., anti-GCGR antibody as described in U.S. Pat. Appln. Pub. No. US2015/0337045A1 or US2016/0075778A1), an anti-VEGF antibody, an anti-IL1R antibody, an interleukin 4 receptor antibody (e.g., an anti-IL4R antibody as described in U.S. Pat. Appln. Pub. No. US2014/0271681A1 or U.S. Pat. No. 8,735,095 or 8,945,559), an anti-interleukin 6 receptor antibody (e.g., an anti-IL6R antibody, as described in U.S. Pat. No. 7,582,298, 8,043,617 or 9,173,880), an anti-IL1 antibody, an anti-IL2 antibody, an anti-IL3 antibody, an anti-IL4 antibody, an anti-IL5 antibody, an anti-IL6 antibody, an anti-IL7 antibody, an anti-interleukin 33 (e.g., anti-IL33 antibody as described in U.S. Pat. Appln. Pub. No. US2014/0271658A1 or US2014/0271642A1), an anti-Respiratory syncytial virus antibody (e.g., anti-RSV antibody as described in U.S. Pat. Appln. Pub. No. US2014/0271653A1), an anti-Cluster of differentiation 3 (e.g., an anti-CD3 antibody, as described in U.S. Pat. Appln. Pub. Nos. US2014/0088295A1 and US20150266966A1, and in U.S. Application No. 62/222,605), an anti-Cluster of differentiation 20 (e.g., an anti-CD20 antibody as described in U.S. Pat. Appln. Pub. Nos. US2014/0088295A1 and US20150266966A1, and in U.S. Pat. No. 7,879,984), an anti-CD19 antibody, an anti-CD28 antibody, an anti-Cluster of Differentiation-48 (e.g., anti-CD48 antibody as described in U.S. Pat. No. 9,228,014), an anti-Fel d1 antibody (e.g., as described in U.S. Pat. No. 9,079,948), an anti-Middle East Respiratory Syndrome virus (e.g., an anti-MERS antibody as described in U.S. Pat. Appln. Pub. No. US2015/0337029A1), an anti-Ebola virus antibody (e.g., as described in U.S. Pat. Appln. Pub. No. US2016/0215040), an anti-Zika virus antibody, an anti-Lymphocyte Activation Gene 3 antibody (e.g., an anti-LAG3 antibody, or an anti-CD223 antibody), an anti-Nerve Growth Factor antibody (e.g., an anti-NGF antibody, as described in U.S. Pat. Appln. Pub. No. US2016/0017029 and U.S. Pat. Nos. 8,309,088 and 9,353,176) and an anti-Activin A antibody. In some embodiments, the bispecific antibody is selected from the group consisting of an anti-CD3×anti-CD20 bispecific antibody (as described in U.S. Pat. Appln. Pub. Nos. US2014/0088295A1 and US20150266966A1), an anti-CD3×anti-Mucin 16 bispecific antibody (e.g., an anti-CD3×anti-Muc16 bispecific antibody), and an anti-CD3×anti-Prostate-specific membrane antigen bispecific antibody (e.g., an anti-CD3×anti-PSMA bispecific antibody). In some embodiments, the protein of interest is selected from the group consisting of alirocumab, sarilumab, fasinumab, nesvacumab, dupilumab, trevogrumab, evinacumab, and rinucumab. All publications mentioned throughout this disclosure are incorporated herein by reference in their entirety.

In other embodiments, the protein of interest is a recombinant protein that contains an Fc moiety and another domain, (e.g., an Fc-fusion protein). In some embodiments, an Fc-fusion protein is a receptor Fc-fusion protein, which contains one or more extracellular domain(s) of a receptor coupled to an Fc moiety. In some embodiments, the Fc moiety comprises a hinge region followed by a CH2 and CH3 domain of an IgG. In some embodiments, the receptor Fc-fusion protein contains two or more distinct receptor chains that bind to either a single ligand or multiple ligands. For example, an Fc-fusion protein is a trap protein, such as for example an IL-1 trap (e.g., rilonacept, which contains the IL-lRAcP ligand binding region fused to the Il-1R1 extracellular region fused to Fc of hIgG1; see U.S. Pat. No. 6,927,004, which is herein incorporated by reference in its entirety), a VEGF trap (e.g., aflibercept or ziv-aflibercept, which contains the Ig domain 2 of the VEGF receptor Flt1 fused to the Ig domain 3 of the VEGF receptor Flk1 fused to Fc of hIgG1; see U.S. Pat. Nos. 7,087,411 and 7,279,159; or conbercept, which contains the Ig domain 2 of the VEGF receptor Flt1 fused to the Ig domain 3 of the VEGF receptor Flk1 fused to the Ig domain 4 of the VEGF receptor Flk1 fused to Fc of hIgG1; see U.S. Pat. No. 8,216,575), or a TNF trap (e.g., etanercept, which contains the TNF receptor fused to Fc of hIgG1; see U.S. Pat. No. U.S. Pat. No. 5,610,279). In other embodiments, an Fc-fusion protein is a ScFv-Fc-fusion protein, which contains one or more of one or more antigen-binding domain(s), such as a variable heavy chain fragment and a variable light chain fragment, of an antibody coupled to an Fc moiety.

Protein Production

A protein of interest can be expressed by a host cell using methods known by those of ordinary skill in the art. Generally, any protein of interest suitable for expression in mammalian cells can be produced by the instant methods, however glycoproteins will especially benefit from the present methods. For example, in specific embodiments the protein of interest is an antibody or antigen-binding fragment thereof, a bispecific antibody or fragment thereof, a chimeric antibody or fragment thereof, an ScFv or fragment thereof, an Fc-tagged protein (e.g., Trap protein) or fragment thereof, a growth factor or a fragment thereof, a cytokine or a fragment thereof, or an extracellular domain of a cell surface receptor or fragment thereof.

Glycoproteins with asparagine-linked (N-linked) glycans are ubiquitous in eukaryotic cells. Biosynthesis of these glycans and their transfer to polypeptides takes place in the endoplasmic reticulum (ER). N-glycan structures are further modified by a number of glycosidases and glycosyl-transferases in the ER and the Golgi complex. Protein production using the present methods is directed at improving consistency of desired N-glycan structure in order to eliminate immunogenic epitopes ("glycotopes"). Detailed structural analysis of glycan-linked proteins may be correlated to functional features of the protein. Such analysis characterizing protein glycosylation typically involves several steps: i) an enzymatic or chemical release of the attached glycans; ii) derivatization of the released glycans via reductive amination with aromatic or aliphatic amines or permethylation; iii) analysis of the glycans. Many variations of analyzing glycosylation patterns in known to the skilled person. Glycoproteins may carry several types of glycoforms occupying various sites in specific quantities, and therefore their complexity may make it difficult to reproduce in certain production methods. Consistency of type and quantity of glycoform is measurable and represents a desirable outcome for therapeutic protein production.

The present disclosure shows that producing numerous batches of a protein of interest in batch or fed-batch culture, by culturing cells expressing the protein of interest in media comprising soy hydrolysate with specific concentrations of ornithine or putrescine result in increased quality of the proteins being produced and improved consistency from batch-to-batch. Therefore, another aspect of the present disclosure provides a plurality of protein preparations that have each been produced by culturing cells in media comprising separate batches of soy hydrolysate containing a predetermined amount of ornithine or putrescine. In certain embodiments, each batch of soy hydrolysate selected for use in cell culture has a concentration of 0.67 mg ornithine or putrescine per g soy or less, particularly from 0.0067 mg to 0.67 mg ornithine or putrescine per g soy, or from 0.0067 to 0.27 mg ornithine or putrescine per g soy.

In other embodiments, the concentration of ornithine or putrescine in a soy hydrolysate-containing cell culture media ranges from 0.5 mg/L to 4.5 mg/L, 0.5 mg/L to 4.0 mg/L, 0.5 mg/L to 3.5 mg/L, 0.5 mg/L to 3.0 mg/L, 0.5 mg/L to 2.5 mg/L, 0.5 mg/L to 2.0 mg/L, 0.5 mg/L to 1.5 mg/L or 0.5 mg/L to 1.0 mg/L. In some embodiments, the concentration of ornithine or putrescine in soy hydrolysate-containing cell culture media ranges from 1.0 mg/L to 5.0 mg/L, 1.5 mg/L to 5.0 mg/L, 2.0 mg/L to 5.0 mg/L, 2.5 mg/L to 5.0 mg/L, 3.0 mg/L to 5.0 mg/L, 3.5 mg/L to 5.0 mg/L, 4.0 mg/L to 5.0 mg/L or 4.5 mg/L to 5.0 mg/L.

In specific embodiments, a cell culture media containing soy hydrolysate includes ornithine or putrescine at an amount of 0.5 mg/L, 0.6 mg/L, 0.7 mg/L, 0.8 mg/L, 0.9 mg/L, 1.1 mg/L, 1.2 mg/L, 1.3 mg/L, 1.4 mg/L, 1.5 mg/L, 1.6 mg/L, 1.7 mg/L, 1.8 mg/L, 1.9 mg/L, 2.0 mg/L, 2.1 mg/L, 2.2 mg/L, 2.3 mg/L, 2.4 mg/L, 2.5 mg/L, 2.6 mg/L, 2.7 mg/L, 2.8 mg/L, 2.9 mg/L, 3.0 mg/L, 3.1 mg/L, 3.2 mg/L, 3.3 mg/L, 3.4 mg/L, 3.5 mg/L, 3.6 mg/L, 3.7 mg/L, 3.8 mg/L, 3.9 mg/L, 4.0 mg/L, 4.1 mg/L, 4.2 mg/L, 4.3 mg/L, 4.4 mg/L, 4.5 mg/L, 4.6 mg/L, 4.7 mg/L, 4.8 mg/L, 4.9 mg/L, or 5.0 mg/L.

In other embodiments, the desired concentration of ornithine or putrescine in a batch of media containing soy hydrolysate is not more than 5.0 mg/L. In still other embodiments, the desired concentration of ornithine or putrescine in a batch of media containing soy hydrolysate is not more than 2.0 mg/L. In another embodiment, the desired concentration of ornithine or putrescine in a batch of media containing soy hydrolysate is not more than 1.8 mg/L. In some embodiments, the desired concentration of ornithine or putrescine in a batch of media containing soy is from 0.5 mg/L to 5.0 mg/L. In still other embodiments, the desired concentration of ornithine or putrescine in a batch of media containing soy hydrolysate falls with the range of 0.5 mg/L to 2.0 mg/L. In yet another embodiment, the desired concentration of ornithine or putrescine in a batch of media containing soy hydrolysate falls with the range of 0.5 mg/L to 1.8 mg/L.

In certain embodiments, quality of the protein of interest or amount of certain glycans produced in each protein preparation of a plurality of protein preparations is improved when compared to a protein preparation produced by a method including culturing cells in media supplemented with soy hydrolysate containing ornithine or putrescine at a concentration of greater than 5 mg/L. In certain embodiments, improved protein quality exhibited by each protein preparation is measured by: the presence or absence of glycosylation at one or more amino acids of the protein of interest, the amount of glycan on the protein of interest, the presence of sialic acid at one or more glycosylation sites on the protein of interest, or a combination thereof. In one embodiment, the protein quality corresponds to the glycosylation state of individual members of a population of proteins produced in culture. In certain embodiments, quality is improved by modulating the glycosylation substitutions present on individual glycoproteins of a population of proteins produced in culture by culturing the cells in media supplemented with soy hydrolysate having a concentration of 5.0 mg/L or less of ornithine or putrescine, from 0.5 mg/L to 5.0 mg/L of ornithine or putrescine, or from 0.5 mg/L to 2.0 mg/L of ornithine or putrescine.

In one embodiment, protein quality is determined by comparing the abundance of at least one glycan molecule in each batch of proteins from a plurality of protein preparations to the abundance of the same glycan molecule(s) in another batch of proteins. The term "abundance" as used herein refers to the percentage of proteins having a particular glycan molecule in a particular production lot, or the amount of proteins having a particular glycan molecule relative to the amount of all types of glycan molecules in a production lot. In some embodiments, the glycan molecule is selected from the group consisting of A1, AIF, A2, A2F, Man5, NA2, NA2F, NA2G1, NA2GIF, NGA2, and NGA2FI. In a specific embodiment, the glycan molecule is A1 (e.g., Peak 11 of FIG. 2).

Proteins of interest produced by the cell culture methods of the instant disclosure display favorable quality characteristics. Protein quality can be measure, for example, by using methods well known to those skilled in the art, such as weak cation exchange chromatography, capillary isoelectric focusing, size-exclusion chromatography, High Performance Liquid Chromatography (HPLC), ELISA, and/or western blot analysis. In some embodiments, protein quality is measured by mass spectrometry, such as capillary electrophoresis mass spectrometry (CE-MS). In specific embodiments, protein quality is determined by comparing mass spectrometry read outs of each batch of proteins from a plurality of protein preparations.

High Performance Liquid Chromatography (HPLC) with fluorescent detection of exemplary production lots show that the proteins of interest (glycoproteins) produced from cells cultured in media including soy hydrolysate with an ornithine or putrescine concentration from 0.5 mg/L to 5.0 mg/L have more consistent glycan expression and glycosylation patterns, as exemplified in Tables 2-4, herein.

Oligosaccharide Profiling

The extent and distribution of specific N-linked sugar chains on glycoproteins can be ascertained by oligosaccharide profiling. In one embodiment, the glycoprotein is deglycosylated with peptide: N-glycosidase F (PNGase F) to cleave and remove the N-linked oligosaccharides from asparagine side chains. The oligosaccharides are then derivatized with a fluorescent reagent, such as anthranilic acid. The sugar chains are then separated by normal phase anion-exchange HPLC and detected with a fluorescence detector, generating an HPLC chromatogram.

In another embodiment, as part of the overall carbohydrate characterization analysis, individual glycopeptides are isolated following trypsin digestion of reduced and alkylated glycoprotein. Individual tryptic glycopeptides are separated by reverse phase HPLC, coupled with a subsequent C18 column for increased resolution as needed. The oligosaccharides are released from each of the separated glycopeptides by PNGase F digestion, derivatized with anthranilic acid, and analyzed by fluorescence HPLC to obtain a site-specific oligosaccharide profile of the glycoprotein. In one embodiment where the glycoprotein is rilonacept (SEQ ID NO: 1), asparagine residues at N37, N87, N91, N98, optionally N176, N189, N279, N418, N511, N551, N567, N581, N615, and N730 are glycosylated. In one embodiment, any one or more of residues N37, N98, N418, and N511 of rilonacept (residue positions correlating to SEQ ID NO: 1) contain an A1 oligosaccharide. In one embodiment where the glycoprotein is aflibercept (SEQ ID NO: 2), asparagine residues at N36, N68, N123, N196, and N282 are glycosylated. In one embodiment, any one or both of residues N123 and N196 of aflibercept (residue positions correlating to SEQ ID NO: 2) contain an A1 oligosaccharide.

In another embodiment, oligosaccharide pools from the glycoprotein are generated by deglycosylation of the proteins with PNGase F, followed by anthranilic acid derivatization and subsequent solid phase extraction (SPE). The masses of oligosaccharides are then measured using MALDI-TOF in a negative linear mode with 2,4,6-trihydroxyacetophenone (THAP) as matrix.

Each observed mass is assigned to a unique oligosaccharide structure based on the masses of commonly observed N-linked glycans in recombinant proteins. The expected mass assignments of all the peaks are summarized in Table 1. The expected masses are the average mass calculated based on the proposed N-linked sugar chain structures with addition of anthranilic acid residue mass. The monosaccharide compositions are listed based on the proposed N-linked sugar chain structures as well.

In another embodiment, a quantitative oligosaccharide fingerprint assay using capillary electrophoresis is used to characterize the N-glycan (oligosaccharide) structure of the subject glycoprotein. The glycoprotein is denatured and then deglycosylated by treatment with PNGase F. Released oligosaccharides are then isolated by precipitation following removal of the protein. Isolated oligosaccharide pools are labeled with the fluorophore 8-aminopyrene 1,3,6-trisulfonate (APTS). Labeled oligosaccharides are then separated by capillary electrophoresis and monitored with a laser induced fluorescence detector using an excitation wavelength of 488 nm and emission wavelength of 520 nm.

Figure 2:
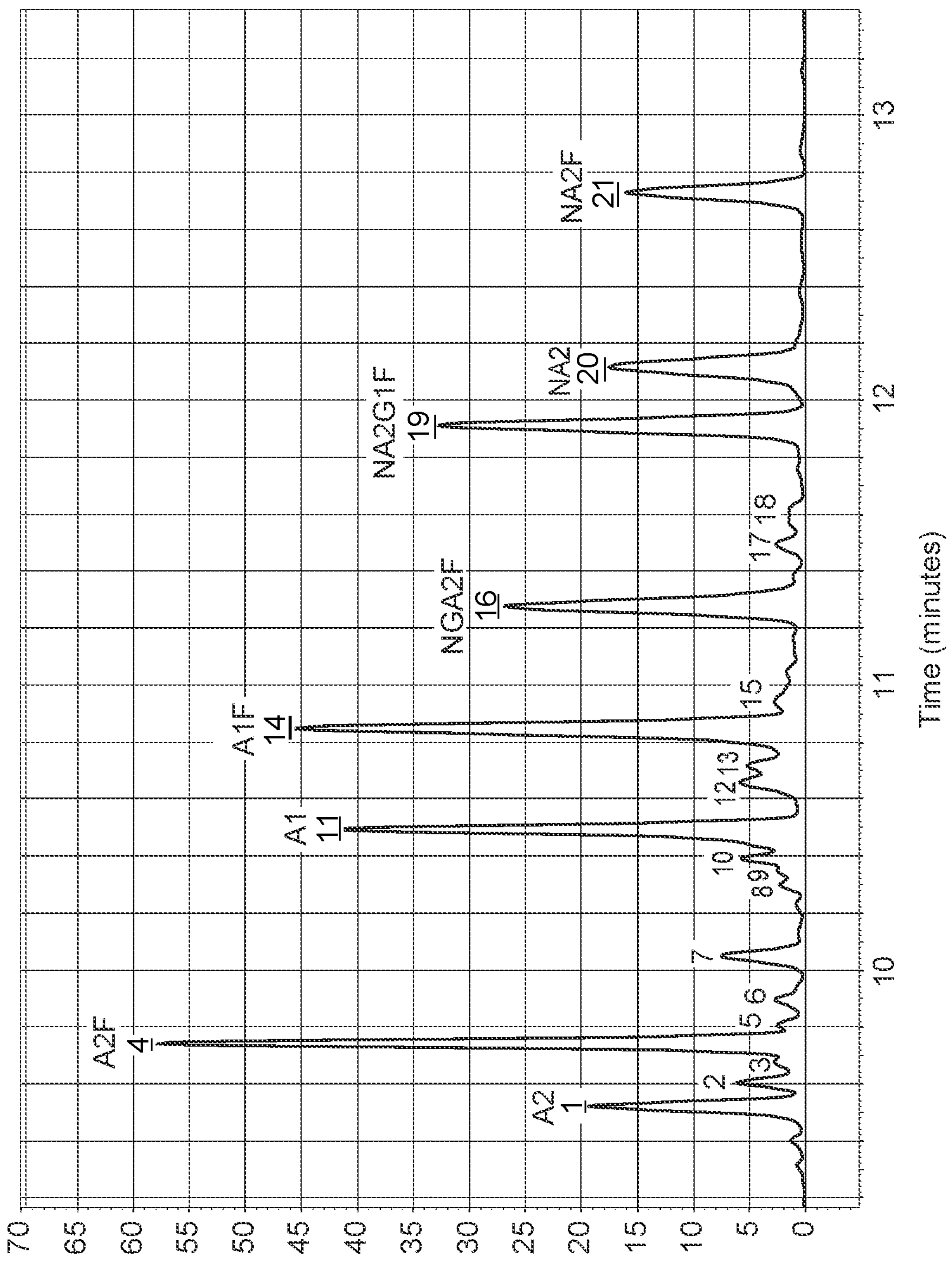
FIG. 2 depicts a capillary electrophoretogram of oligosaccharides released from a glycoprotein by peptide: N-glycosidase F (PNGase F) digestion. The X-axis depicts time of elution from a capillary, and the Y-axis depicts light absorbance or fluorescence intensity. The peaks are numbered 1-21. Peak 1 represents the N-glycan A2; peak 4 represents the N-glycan A2F; peak 11 represents the N-glycan A1; peak 14 represents the N-glycan A1F; peak 16 represents the N-glycan NGA2F; peak 19 represents the N-glycan NA2GIF; peak 20 represents the N-glycan NA2; and peak 21 represents the N-glycan NA2F.

An electropherogram is generated, as depicted in FIG. 2 for the aflibercept glycoprotein, with all quantifiable peaks numbered (total of 21 peaks in this example). The complete integrated peak area (total peak area) for the oligosaccharide fingerprint is determined. The relative amount of each oligosaccharide can be determined by dividing the peak area for that particular oligosaccharide (e.g., A1 peak area) by the total peak area.

In some embodiments, the quality of the subject glycoprotein is assessed by determining the level of sialylation (the amount of sialic residues per glycoprotein) or fucosylation (the amount of fucose residues per glycoprotein). In one embodiment, the total number of sialic acids on a glycoprotein are determined using a quantitative HPLC assay. In this assay, the sialic acids are released from the glycoprotein using mild acid hydrolysis, then derivatized with o-Phenylenediamine, separated by HPLC, and detected with either UV or fluorescence detectors. Quantitation of sialic acid can be assessed relative to a standard curve using e.g., sialyllactose. The sialic acid content is calculated from the moles of sialic acid released and the moles of the glycoprotein used in the reaction.

In one embodiment, the sialic acid content of the rilonacept glycoprotein is about 30-70 moles sialic acid per 1 mole of glycoprotein (mol/mol), about 35-65 mol/mol, 30 mol/mol, 31 mol/mol, 32 mol/mol, 33 mol/mol, 34 mol/mol, 35 mol/mol, 36 mol/mol, 37 mol/mol, 38 mol/mol, 39 mol/mol, 40 mol/mol, 41 mol/mol, 42 mol/mol, 43 mol/mol, 44 mol/mol, 45 mol/mol, 46 mol/mol, 47 mol/mol, 48 mol/mol, 49 mol/mol, 50 mol/mol, 51 mol/mol, 52 mol/mol, 53 mol/mol, 54 mol/mol, 55 mol/mol, 56 mol/mol, 57 mol/mol, 58 mol/mol, 59 mol/mol, 60 mol/mol, 61 mol/mol, 62 mol/mol, 63 mol/mol, 64 mol/mol, 65 mol/mol, 66 mol/mol, 67 mol/mol, 68 mol/mol, 69 mol/mol, or 70 mol/mol.

In one embodiment, the sialic acid content of the aflibercept glycoprotein is about 5-15 moles sialic acid per 1 mole of glycoprotein (mol/mol), about 8-12 mol/mol, 4 mol/mol, 5 mol/mol, 6 mol/mol, 7 mol/mol, 8 mol/mol, 9 mol/mol, 10 mol/mol, 11 mol/mol, 12 mol/mol, 13 mol/mol, 14 mol/mol, 15 mol/mol, 16 mol/mol, 17 mol/mol, 18 mol/mol, 19 mol/mol, or 20 mol/mol.

In one embodiment, oligosaccharide profiling is employed to determine the extent and distribution of sialylation of N-linked sugar chains on the glycoprotein. The glycoprotein is deglycosylated with PNGase F, and then derivatized with the fluorescent reagent, anthranilic acid. The oligosaccharides are then separated by normal phase anion-exchange HPLC and detected with a fluorescence detector to generate an HPLC chromatogram of the oligosaccharide profile. The Z number (which measures the average degree of sialylation) for the glycoprotein is calculated from the following formula:

(OS A*O)+(ISA*111-(2SA*2)+(3SA*3)+ . . .
(nSA*n)1/(OSA+15A+2SA+35A+ . . . n5A)

To determine the Z number, the area of each peak from the oligosaccharide profile is integrated. The total sialic acid is calculated as the sum of the areas of the 0 sialic acid/chain peaks multiplied by 0, the 1 sialic acid/chain peaks multiplied by 1, the 2 sialic acid/chain peaks multiplied by 2, and the 3 sialic acid/chain peaks multiplied by 3, etc. The total number of sugar chains is generated as the sum of the areas of all of the peaks. The Z number is the total sialic acid area divided by the total sugar chain area.

In one embodiment, the sialic acid Z number of the rilonacept glycoprotein is about 1.3-1.6, 1.4-1.5, 1.41-1.48, 1.3, 1.31, 1.32, 1.33, 1.34, 1.35, 1.36, 1.37, 1.38, 1.39, 1.4, 1.41, 1.42, 1.43, 1.44, 1.45, 1.46, 1.47, 1.48, 1.49, 1.5, 1.51, 1.52, 1.53, 1.54, 1.55, 1.56, 1.57, 1.58, 1.59, or 1.60.

In one embodiment, the sialic acid Z number of the aflibercept glycoprotein is about 0.5-2, 1-1.5, 1-1.2, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.86, 0.87, 0.88, 0.89, 0.9, 0.91, 0.92, 0.93, 0.94, 0.95, 0.96, 0.97, 0.98, 0.99, 1, 1.01, 1.02, 1.03, 1.04, 1.05, 1.06, 1.07, 1.08, 1.09, 1.1, 1.11, 1.12, 1.13, 1.14, 1.15, 1.16, 1.17, 1.18, 1.19, 1.2, 1.21, 1.22, 1.23, 1.24, 1.25, 1.26, 1.27, 1.28, 1.29, or 1.3.

EXAMPLES

The following examples are put forth so as to provide those of ordinary skill in the art how to make and use the methods and compositions described herein, and are not intended to limit the scope of what the inventors regard as their invention. Efforts have been made to ensure accuracy with respect to numbers used (e.g., amount, temperature, etc.) but some experimental error and deviation should be accounted for. Unless indicated otherwise, parts are parts by weight, molecular weight is average molecular weight, temperature is in degrees Centigrade, and pressure is at or near atmospheric.

Example 1: Screening Soy Hydrolysate to Determine Amino Acid Concentration

A soy hydrolysate sample was weighed and a 20 gram portion thereof was dissolved in 1 L water to a starting concentration of 20 g/L. The resulting soy hydrolysate solution was then further diluted in water to a desired concentration for use in cell culture and the molecular composition of the resulting soy hydrolysate solution was determined using by chromatography.

The concentration of amino acids in the soy hydrolysate sample was measured by chromatography on an ion exchange column with post column ninhydrin detection. See, e.g., Moore and Stein. J. Biol. Chem. (1954) Vol. 211 pp. 907-913. Soy hydrolysate samples were diluted to permit sensitive separation and resolution of individual peaks (amino acids) as eluted from the HPLC column and compared to a standard. Each peak area of the chromatogram, as shown in FIGS. 1A and 1B, was compared to a standard to determine concentration of each eluate.

To determine whether a batch of soy hydrolysate powder contains less than 0.67 milligram ornithine or putrescine per gram soy, the chromatogram of each representative sample is compared to a standard. For example, FIG. 1A shows a batch of soy hydrolysate with an eluate containing ornithine at retention time 89.02, which reveals a peak area equivalent to 1.57 mg ornithine per g soy of ornithine, as compared to the standard. FIG. 1B illustrates a batch of soy hydrolysate having an ornithine concentration of less than 0.67 mg ornithine per g soy. Batches of soy hydrolysate with between 0.067 and 0.67 mg ornithine per g soy were selected for use in cell culture methods to produce biotherapeutic proteins with more consistent protein glycosylation from lot-to lot. However, soy hydrolysate batches containing ornithine at a concentration greater than less than 0.67 mg ornithine per g soy were employed in further experiments, as described below, to determine the effects of soy hydrolysate ornithine concentration on protein production.

Example 2: Expression and Glycosylation Profile of a Protein of Interest

CHO cells expressing a trap protein (receptor-Fc fusion protein, VEGF-trap) were cultured in proprietary medium including soy hydrolysate containing varying amounts of ornithine, putrescine and citrulline, or a combination thereof, in order to determine which amino acid components affect the quality of proteins produced. Table 2, shows that the levels of ornithine in the hydrolysate correlate negatively with the quality of protein production lots, as indicated by the increased area under the curve for a key N-glycan for protein lots produced as a result of culturing CHO cells in media supplemented with soy hydrolysate containing ornithine at a concentration less than 5.0 mg/L independent of citrulline concentration.

Figure 3:
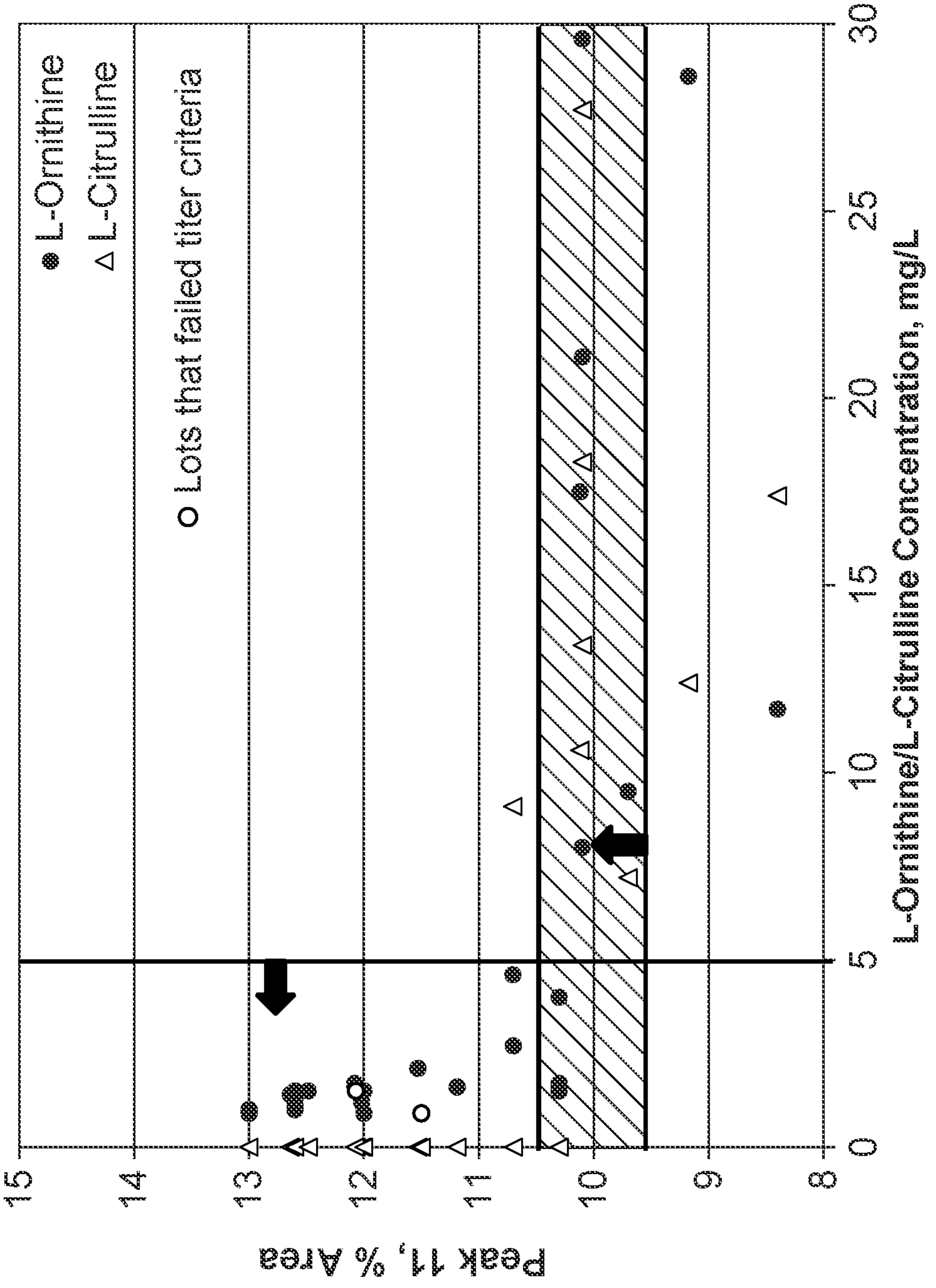
FIG. 3 depicts a dot blot of the relative amount of A1 N-glycan as a function of ornithine and citrulline concentration in soy protein hydrolysate. The X-axis depicts the concentration of citrulline or ornithine in mg/L. The Y-axis depicts the relative area of peak 11, which represents A1 N-glycan.

As shown in Table 2 and depicted in FIG. 3, VEGF-trap protein product lots produced by cells cultured in media including soy hydrolysate with an ornithine concentration of 2.0 mg/L or less produce higher quality protein product, when compared to cells cultured in media comprising more than 5.0 mg/L of ornithine, citrulline or putrescine.

TABLE 2

| Soy amino acid concentration | A1 N-Glycan relative amount (% area under the curve) |
|---|---|
| 1.6 mg/L ornithine | 12.5 |
| 6.6 mg/L ornithine | 9.8 |
| 31.6 mg/L ornithine | 9.3 |
| 36.6 mg/L putrescine | 9.0 |
| 1.6 mg/L ornithine; 0 mg/L citrulline | 12.0 |
| 1.6 mg/L ornithine; 30 mg/L citrulline | 11.5 |
| 31.6 mg/L ornithine; 0 mg/L citrulline | 8.8 |

Detailed glycan analysis was performed using chromatography based on well-known methods for HPLC and fluorescent anthranilic acid (AA) tags (Anumula, and Dhume, Glycobiology (1998) 8 (7) pp. 685-694) for each lot of glycoprotein to determine whether ornithine had an impact on protein glycosylation profiles. As shown in Table 3, culturing cells in media that includes soy hydrolysate comprising less than or equal less than 0.67 mg ornithine per g soy results in more consistent protein production from lot-to-lot. More specifically, ~90% of production lots cultured in medium comprising selected soy hydrolysate meet FDA production criteria. In contrast, only 57% of production lots cultured in medium comprising soy hydrolysate having more than 5 mg/L ornithine meet FDA production criteria (area under the curve for a specific N-glycan peak). As shown in Table 3, VEGF-trap protein product lots produced by cells cultured in medium including soy hydrolysate with an ornithine concentration of 0.67 mg ornithine per g soy or less exhibit increased product quality and more consistent quality from lot-to-lot.

TABLE 3

| mg ornithine per g soy | Lots with glycan amount greater than 10.5% (quality parameter) | Suitable protein product lots | Failed protein product lots |
|---|---|---|---|
| ≤0.67 | 21 | 19/21 | 2/21 |
| >0.67 | 4 | 4/7 | 3/7 |

Each production lot was also compared (with respect to glycan profile) to a reference standard which represents a therapeutically acceptable batch of protein for the exemplary VEGF-trap protein. Representative glycan analysis is shown in Table 4 for protein lots produced from cells cultured in medium supplemented with soy hydrolysate resulting in final concentration of ornithine between 0.5 mg/L and 2.0 mg/L. Compared to the reference, each produced trap protein comprises a consistent glycan profile having peaks within an acceptable range (75% of lots analyzed). In contrast, each lot produced by cells cultured in medium supplemented with soy hydrolysate comprising over 5.0 mg/L ornithine failed to meet FDA acceptance criteria. As shown in Table 4, Protein product lots produced by cells cultured in media including soy hydrolysate with an ornithine concentration from 0.5 mg/L to 2.0 mg/L or less produce higher quality lots, as demonstrated by A1 N-glycan levels falling below product acceptance criteria, than cells cultured in media comprising more soy hydrolysate having an ornithine concentration greater than 5.0 mg/L.

TABLE 4

| Glycan | A2 | A2F | A1 | A1F | NGA2F | NA2G1F | NA2 | NA2F | ornithine (mg/L) |
|---|---|---|---|---|---|---|---|---|---|
| Product lot acceptance criteria (% area under curve) | 4-9 | 10-23 | 10-17 | 11-19 | 5-17 | 8-13 | 4-11 | 2-8 | — |
| Soy hydrolysate batch # 1 | 6.4 | 15.2 | 12.5 | 14.1 | 9.9 | 9.6 | 6.7 | 4.4 | 1.8 |
| Soy hydrolysate batch # 2 | 7.0 | 16.8 | 13.2 | 13.9 | 9.6 | 9.9 | 6.7 | 4.1 | 0.5 |
| Soy hydrolysate batch # 3 | 7.0 | 18.5 | 11.9 | 13.5 | 9.5 | 10.2 | 5.9 | 4 | 1.5 |
| Soy hydrolysate batch # 4 | 9.7 | 18.1 | 14.7 | 11.0 | 8.5 | 9.5 | 5.5 | 3.6 | 0.6 |
| Soy hydrolysate batch # 5 | 6.0 | 16.6 | 9.8 | 13.5 | 11.6 | 9.9 | 5.8 | 4.3 | 13.6 |
| Soy hydrolysate batch # 6 | 5.6 | 15.7 | 9.2 | 14.2 | 12.1 | 10.5 | 6.3 | 4.5 | 28.6 |

Figure 4:
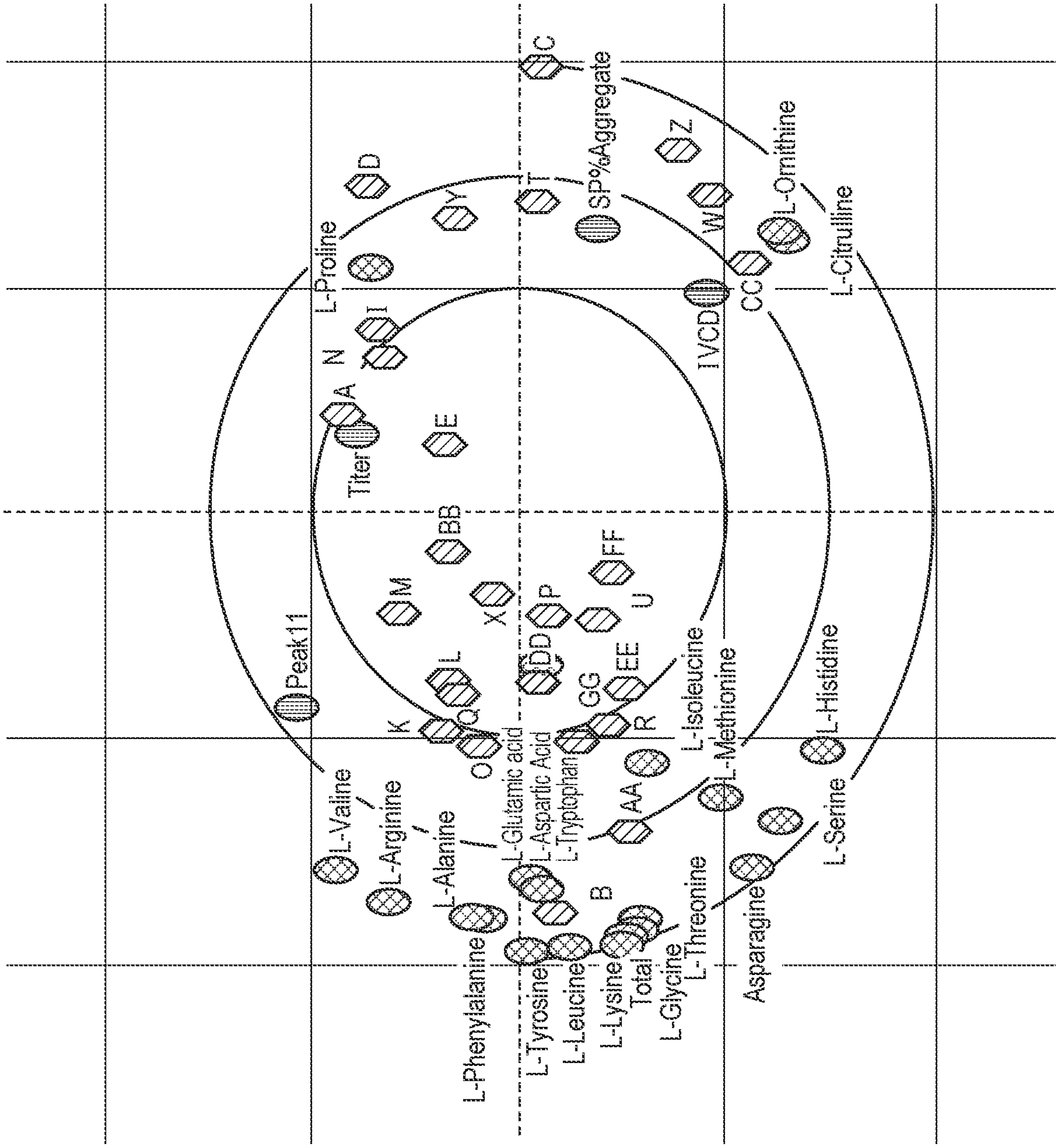
FIG. 4 is a correlation plot depicting the negative correlation of ornithine concentration in soy hydrolysate (lower right quadrant) to the relative amount of peak 11 in aflibercept (A1 N-glycan, upper left quadrant).

FIG. 4 shows the strong negative correlation between the level of ornithine in soy hydrolysate and glycoprotein (aflibercept) quality as demonstrated by A1 N-glycan levels.

Figure 5:
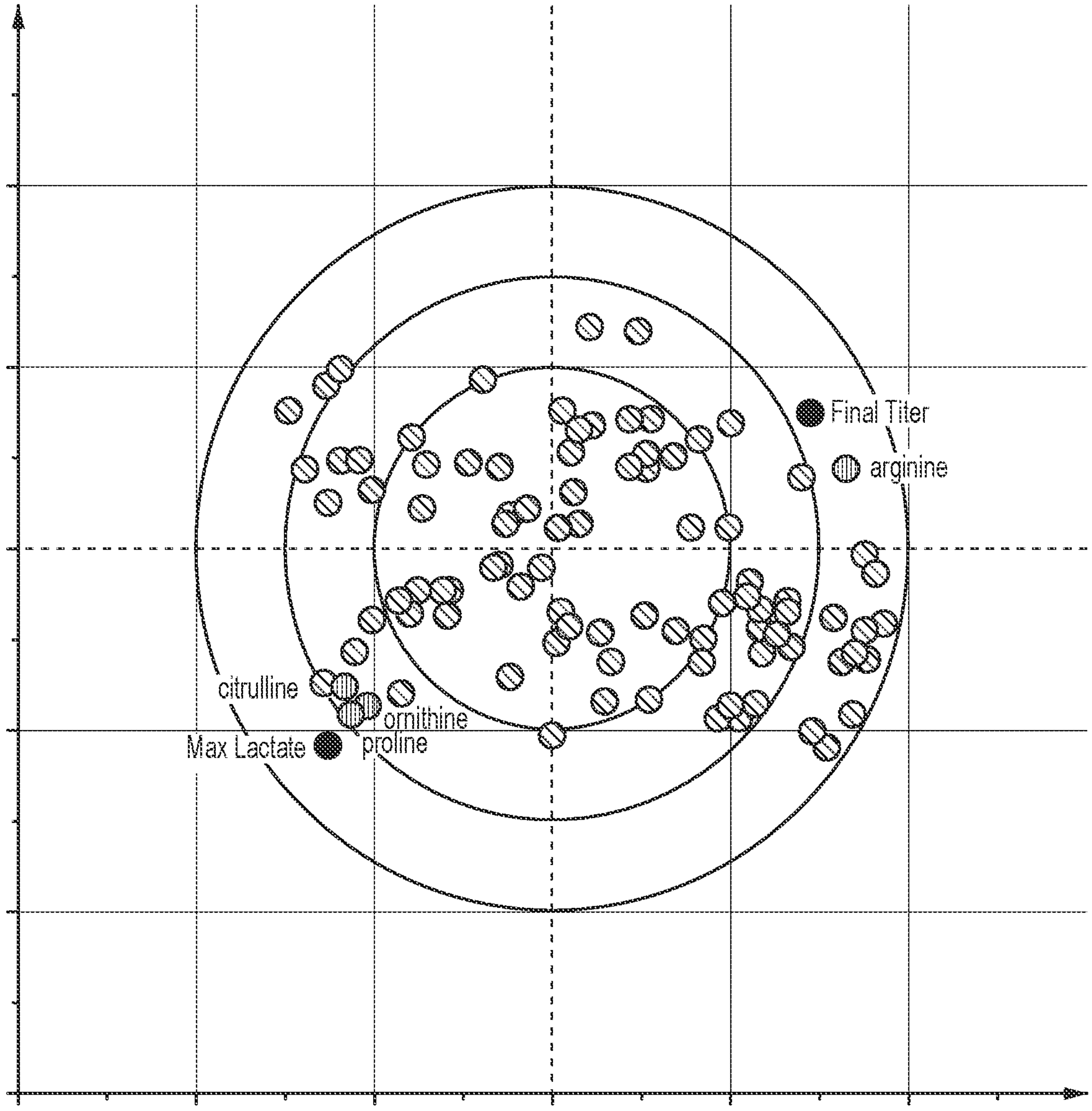
FIG. 5 is a correlation plot depicting (i) the negative correlation of ornithine concentration in soy hydrolysate (lower left quadrant) to the final titer of rilonacept (upper right quadrant); and (ii) the positive correlation of ornithine concentration in soy hydrolysate (lower left quadrant) to the accumulation of lactate in media (lower left quadrant).

Example 3: Glycoprotein Production Titer 16 soy hydrolysate lots were tested for their ability to affect the metabolomics of CHO cell production of rilonacept. Approximately 426 soy hydrolysate analytes were measured and compared to final glycoprotein titer and lactate metabolism. FIG. 5 depicts the loading plots of correlations between the soy hydrolysate analytes and maximum lactate and final glycoprotein titer. The determinations of lactate and glycoprotein titer demonstrate a negative correlation of ornithine in the soy hydrolysate.

Example 4: Marker Confirmation with Spiking Study

Figure 6A:
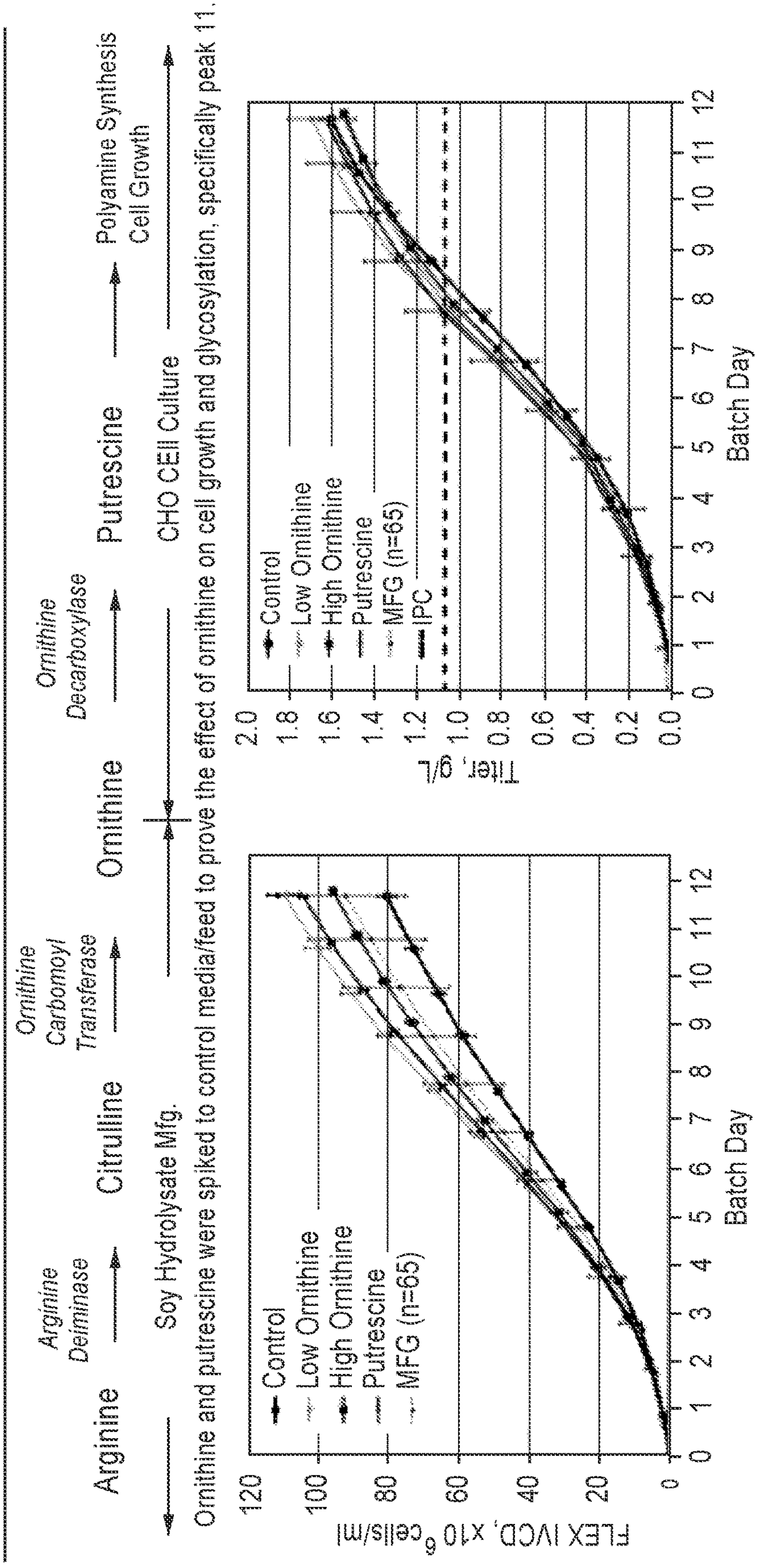
FIG. 6A is a pair of graphs depicting the amount of polyamine synthesized from a CHO cell culture, depicted as either IVCD×$10^6$ cell-day/ml or as titer (as grams per ml) as a function of batch day under various conditions including, control, high and low ornithine concentrations, putrescine, MFC and IPC.

FIGS. 6A and 6B depict CHO cell cultures under control media and feed conditions that received a spike of either ornithine or putrescine to demonstrate the effect of ornithine and putrescine, respectively, on cell growth and glycosylation. Table 6B highlights the effect at peak 11, which is particularly pronounced.

Having described embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method comprising:

(a) determining an amount of ornithine in a soy hydrolysate;

(b) selecting a soy hydrolysate comprising 0.003%-0.027% (w/w) ornithine; and (c) culturing a population of Chinese hamster ovary (CHO) cells expressing a receptor Fc fusion protein in a cell culture medium comprising the soy hydrolysate selected in step (b), such that the amount of ornithine in the culture medium is less than or equal to 5 mg/L to produce the receptor Fc fusion protein.

2. The method of claim 1, wherein the population of cells is obtained by clonal expansion of a cell expressing the receptor Fc fusion protein.

3. The method of claim 1, wherein the cell culture medium comprises 0.6-3 mg/L ornithine.

4. The method of claim 1, wherein the receptor Fc fusion protein is selected from the group consisting of etanercept, rilonacept, and aflibercept.

5. The method of claim 1, wherein the receptor Fc fusion protein comprises an (SA)(Gal)2(GlcNAc)2(Man)3(GlcNAc)3(A1) N-glycan and at least one other N-glycan species, and wherein the relative amount of A1 N-glycan is ≥10% (w/w) of a total amount of all N-glycan species of the glycoprotein.

6. The method of claim 5, wherein the receptor Fc fusion protein further comprises an (SA)2(Gal)2(GlcNAc)2(Man)3(GlcNAc)3(A2) N-glycan, an (SA)2(Gal)2(GlcNAc)2(Man)3(GlcNAc)3(Fuc) (A2F) N-glycan, an (SA)(Gal)2(GlcNAc)2(Man)3(GlcNAc)3(Fuc) (A1F) N-glycan, an (GlcNAc)2(Man)3(GlcNAc)2(Fuc) (NGA2F) N-glycan, an (Gal)(GlcNAc)2(Man)3(GlcNAc)3(Fuc) (NA2G1F) N-glycan, an (Gal)2(GlcNAc)2(Man)3(GlcNAc)3(NA2) N-glycan, and an (Gal)2(GlcNAc)2(Man)3(GlcNAc)3(Fuc) (NA2F) N-glycan.

7. The method of claim 5, wherein the relative amount of the A1 N-glycan is determined by comparing the area under the peak of the A1 N-glycan to the total areas under the peak for all N-glycans of an oligosaccharide fingerprint obtained by capillary electrophoresis.

8. The method of claim 5, wherein the relative amount of the A1 N-glycan is between 10%-17% (w/w).

9. The method of claim 1, comprising:

a. purifying the receptor Fc fusion protein;

b. subjecting the purified receptor Fc fusion protein to oligosaccharide fingerprint analysis; and c. determining the relative amount of an A1 N-glycan compared to total amount of N-glycan species of the receptor Fc fusion protein;

wherein the soy hydrolysate comprising 0.003%-0.027% (w/w) ornithine produces a receptor Fc fusion protein with at least 10% (w/w) A1 N-glycan compared to a total amount of N-glycan species of the receptor Fc fusion protein.

10. The method of claim 9, wherein the receptor Fc fusion protein comprises 8-12 moles of sialic acid per mole of receptor Fc fusion protein, or 35-65 moles of sialic acid per mole of receptor Fc fusion protein.

11. The method of claim 1, wherein the receptor Fc fusion protein is rilonacept with 35-65 moles of sialic acid per mole of Fc receptor fusion protein.

12. The method of claim 11, wherein the rilonacept comprises an A1 N-glycan at any one or more of residues N37, N98, N418, and N511 of SEQ ID NO: 1.

13. The method of claim 1, wherein the Fc receptor fusion protein is aflibercept with 8-12 moles of sialic acid per mole of Fc receptor fusion protein.

14. The method of claim 13, wherein the aflibercept comprises an A1 N-glycan at any one or more of residues N123 and N196 of SEQ ID NO: 2.

15. The method of claim 1, wherein the CHO cells comprise CHO-K1 cells.

16. The method of claim 1, wherein the receptor Fc fusion protein comprises a VEGF Trap protein.

* * * * *